United States Patent
Imamura

(10) Patent No.: US 10,383,514 B2
(45) Date of Patent: Aug. 20, 2019

(54) OPHTHALMOLOGIC IMAGING APPARATUS, OPERATION METHOD THEREOF, AND COMPUTER PROGRAM

(71) Applicant: CANON KABUSHIKI KAISHA, Tokyo (JP)

(72) Inventor: Hiroshi Imamura, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/570,671

(22) PCT Filed: Mar. 30, 2016

(86) PCT No.: PCT/JP2016/001849
§ 371 (c)(1),
(2) Date: Oct. 30, 2017

(87) PCT Pub. No.: WO2016/174823
PCT Pub. Date: Nov. 3, 2016

(65) Prior Publication Data
US 2018/0289258 A1    Oct. 11, 2018

(30) Foreign Application Priority Data
Apr. 30, 2015 (JP) .................. 2015-093539

(51) Int. Cl.
*A61B 3/10* (2006.01)
*A61B 3/12* (2006.01)

(52) U.S. Cl.
CPC ............ *A61B 3/1025* (2013.01); *A61B 3/102* (2013.01); *A61B 3/1225* (2013.01); *A61B 2576/02* (2013.01)

(58) Field of Classification Search
CPC ..... A61B 3/1025; A61B 3/1225; A61B 3/102; A61B 2576/02
USPC ......................... 351/200, 205, 206
See application file for complete search history.

(56) References Cited

FOREIGN PATENT DOCUMENTS

| EP | 2382914 A1 | 11/2011 |
|---|---|---|
| EP | 2749205 A1 | 7/2014 |
| JP | 2001-070247 A | 3/2001 |
| JP | 2010-35607 A | 2/2010 |

OTHER PUBLICATIONS

Scoles, Drew "in vivo imaging of human cone photoreceptor inner segments", IOVS Jul. 2014, vol. 55 No. 7, pp. 4244-4251.
Sulai, Yusufu, "visualization of retinal vascular structure and perfusion with a nonconfocal adaptive optics scanning light ophthalmoscope" J. Opt. Soc. Am. A.vol. 31, No. 3, Mar. 2014 pp. 569-579.

*Primary Examiner* — Tuyen Tra
(74) *Attorney, Agent, or Firm* — Canon U.S.A., Inc. IP Division

(57) ABSTRACT

An ophthalmologic imaging apparatus acquires a plurality of types of images of an eye including a confocal image and a non-confocal image of the eye. The ophthalmologic imaging apparatus includes a deciding unit configured to decide conditions relating to acquisition of the plurality of types of images, for each type of the plurality of types of images, and a control unit configured to control the ophthalmologic imaging apparatus to acquire at lest one of the plurality of types of images, in accordance with the decided conditions.

34 Claims, 16 Drawing Sheets

[Fig. 1]
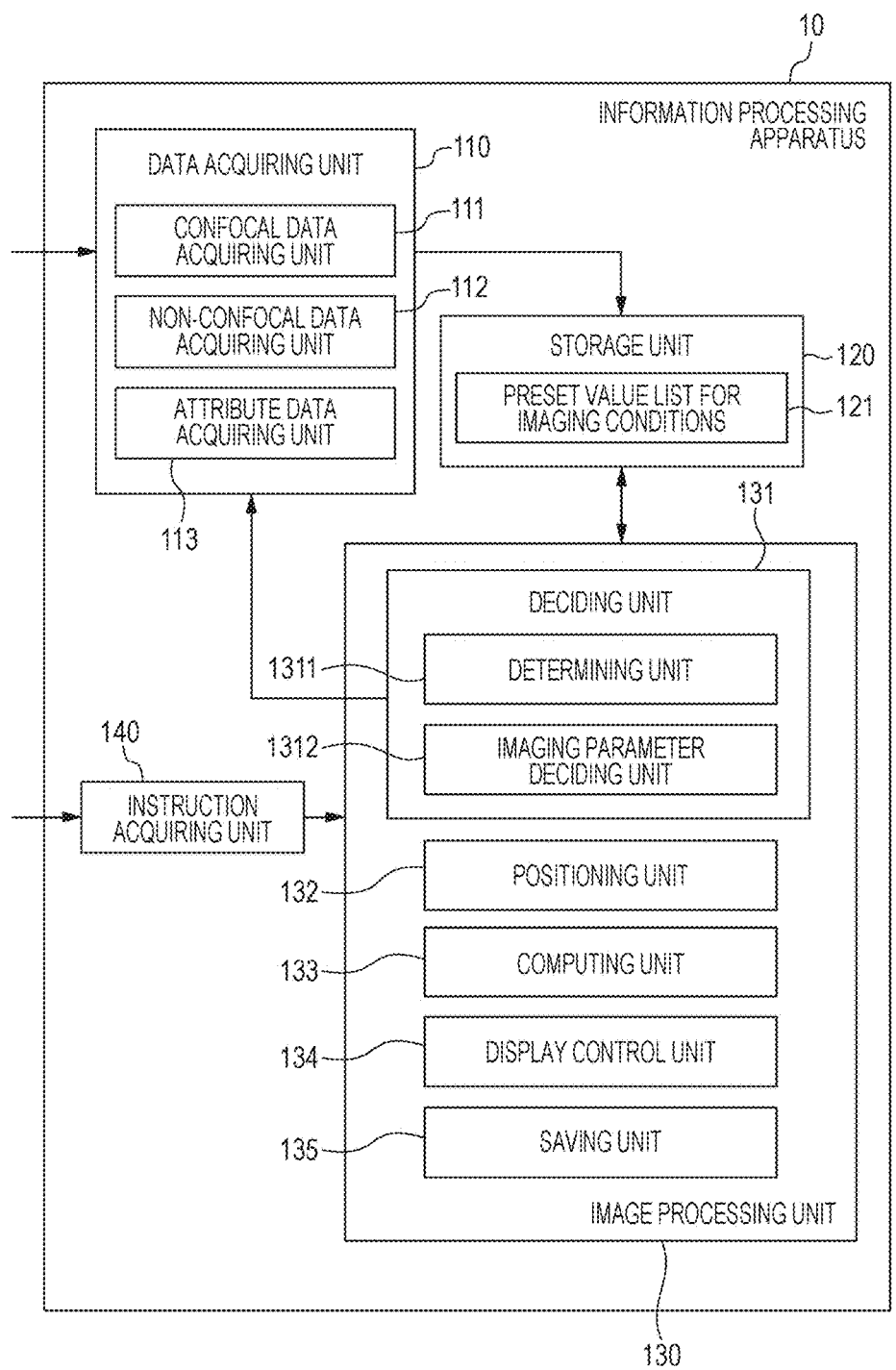

[Fig. 2A]
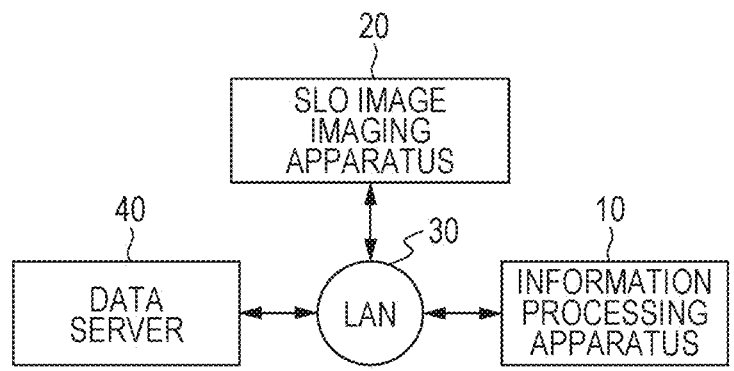
[Fig. 2B]
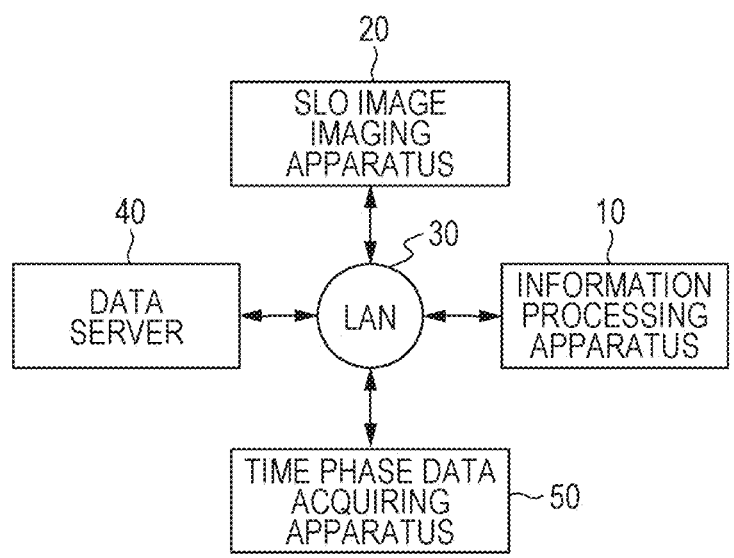

[Fig. 3A]
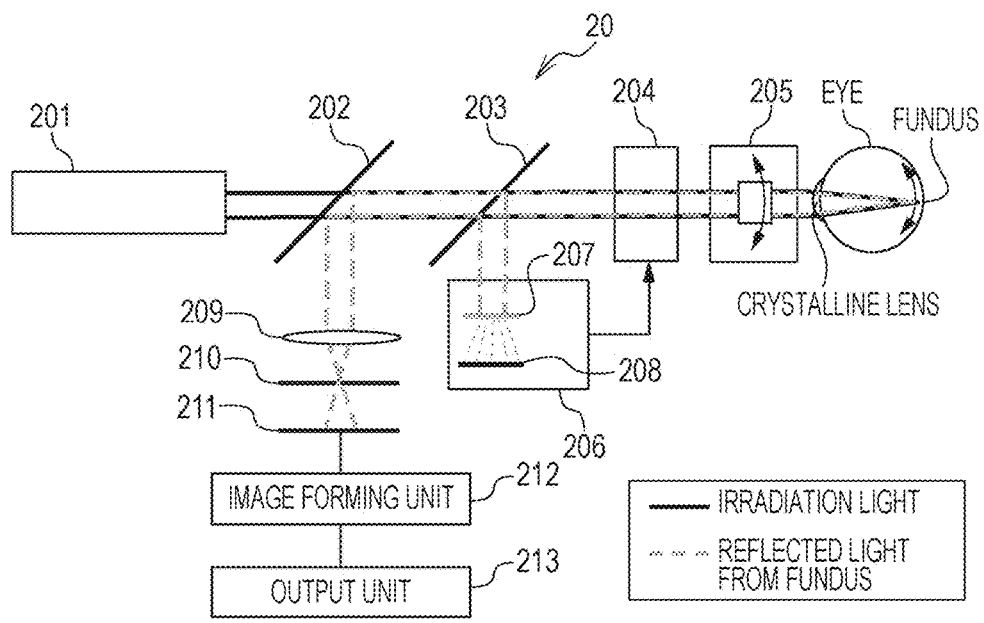
[Fig. 3B]
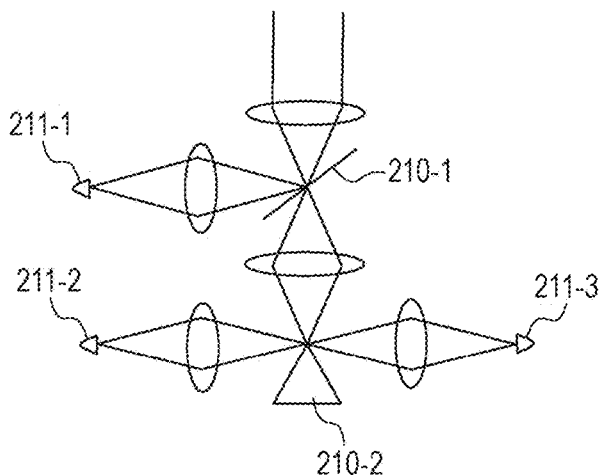
[Fig. 3C]

[Fig. 3D]
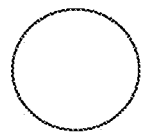
[Fig. 3E]
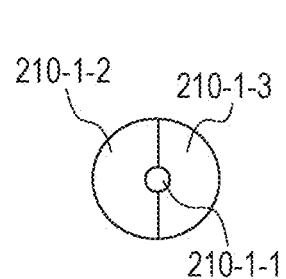
[Fig. 3F]
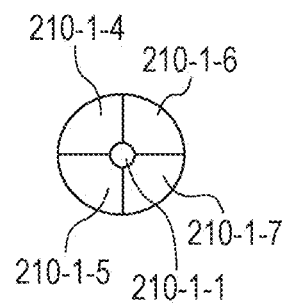
[Fig. 3G]
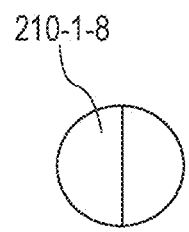
[Fig. 3H]
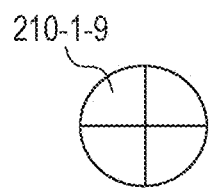

[Fig. 4]
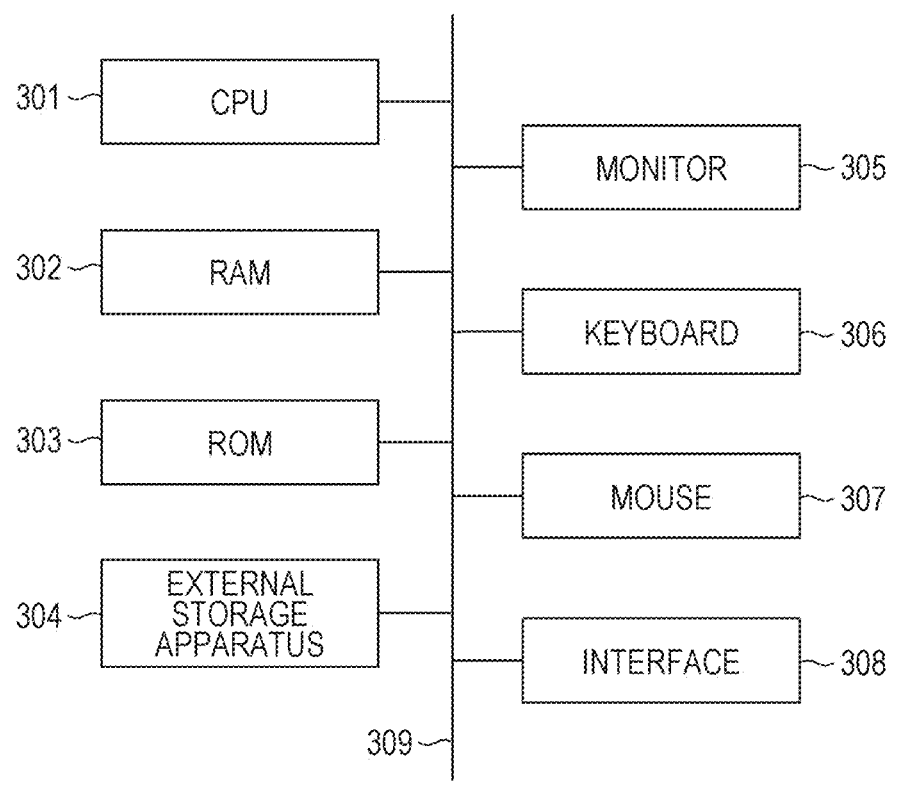

[Fig. 5A]
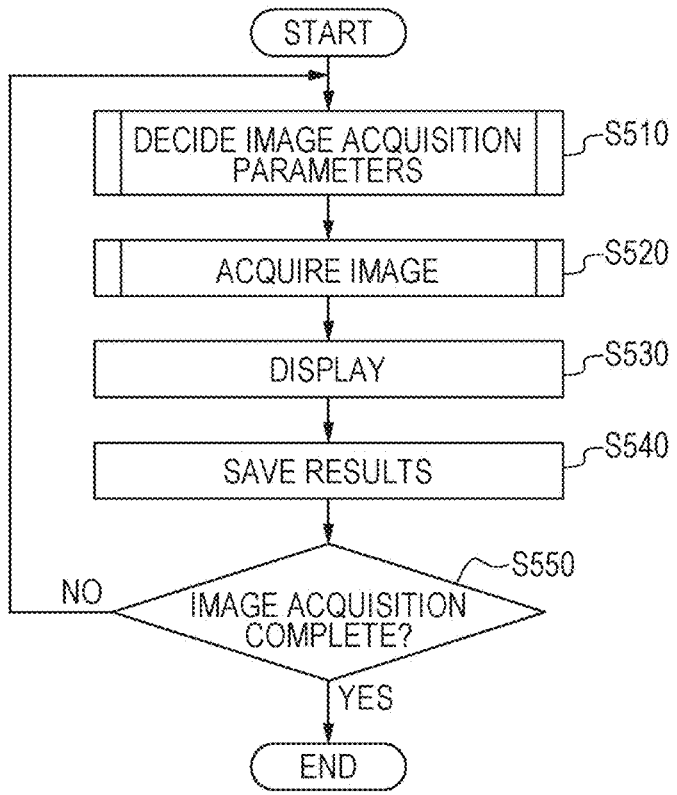
[Fig. 5B]
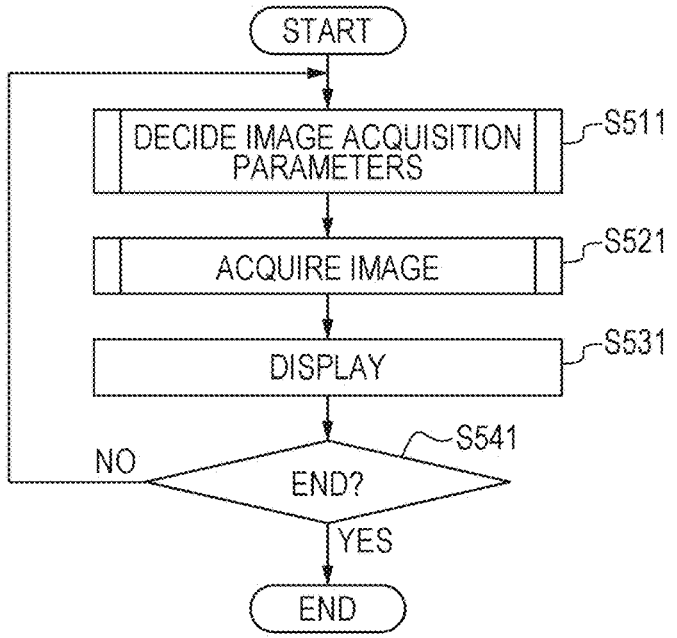

[Fig. 6A]
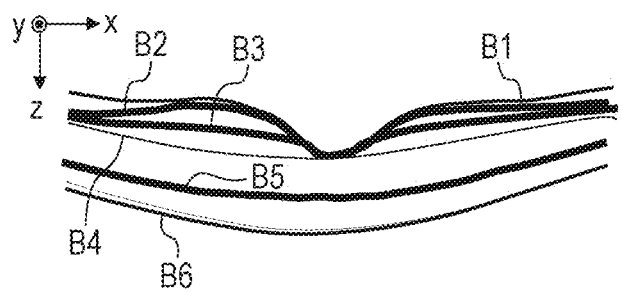
[Fig. 6B]
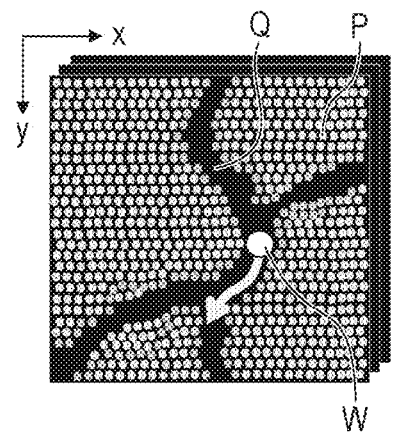

[Fig. 6C]
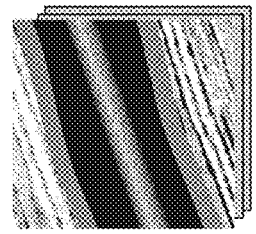
[Fig. 6D]
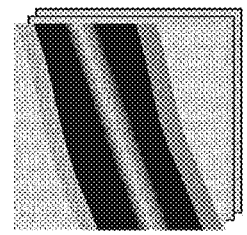
[Fig. 6E]
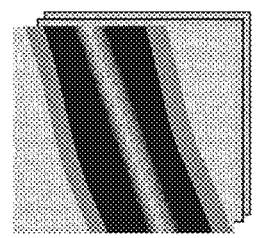
[Fig. 6F]
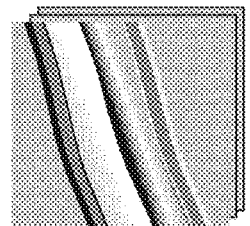
[Fig. 6G]
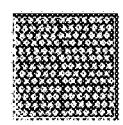

[Fig. 6H]
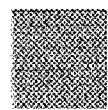
[Fig. 6I]
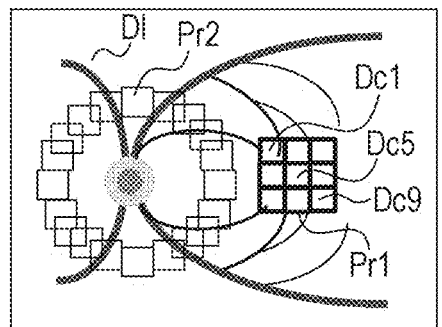
[Fig. 6J]
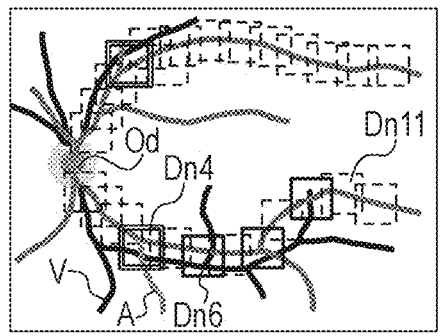

[Fig. 6K]
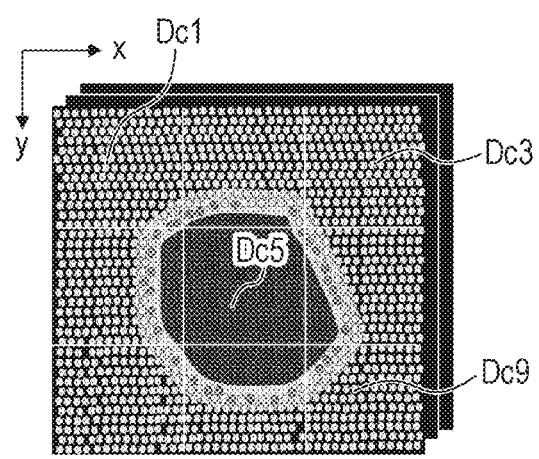
[Fig. 6L]
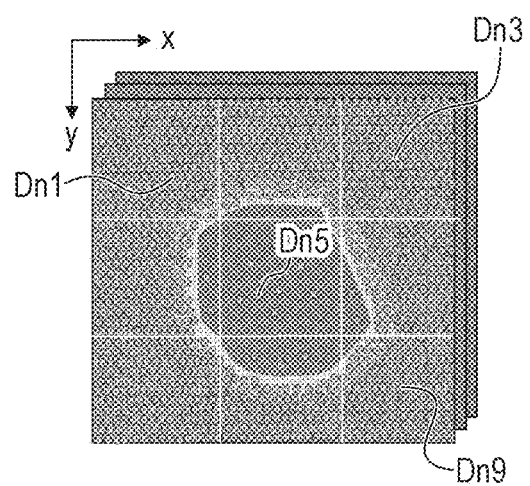

[Fig. 7A]
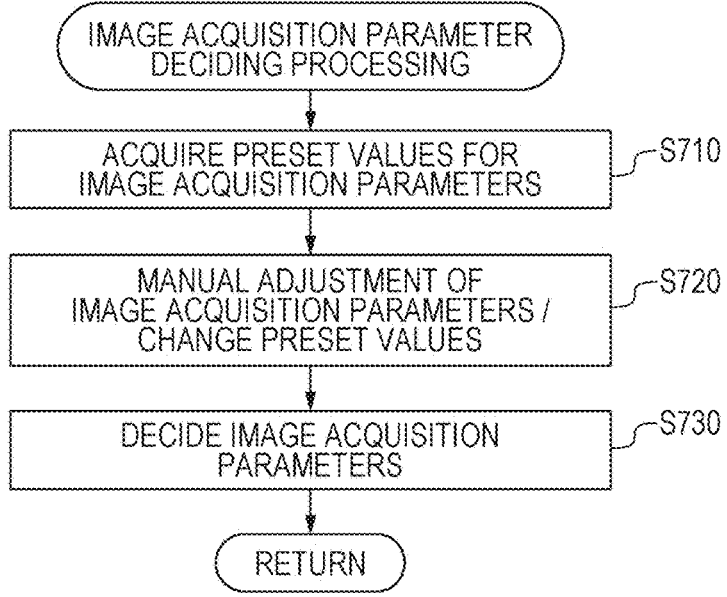
[Fig. 7B]
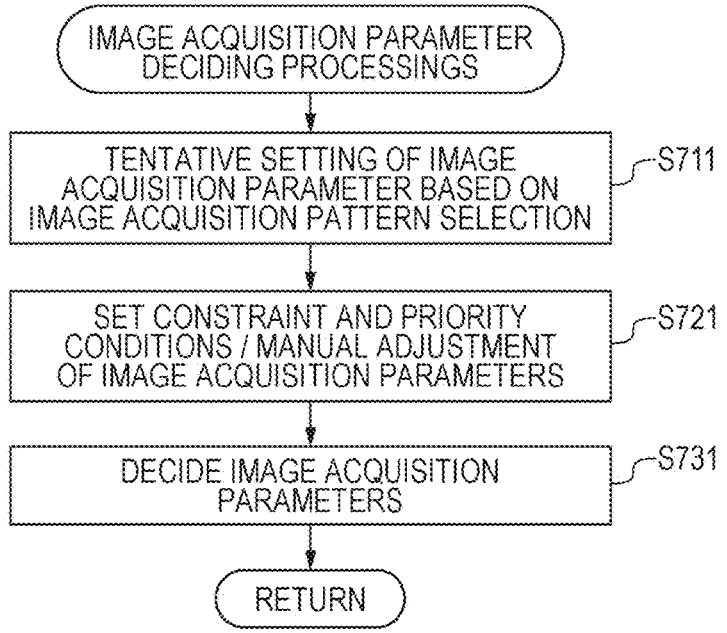

[Fig. 7C]
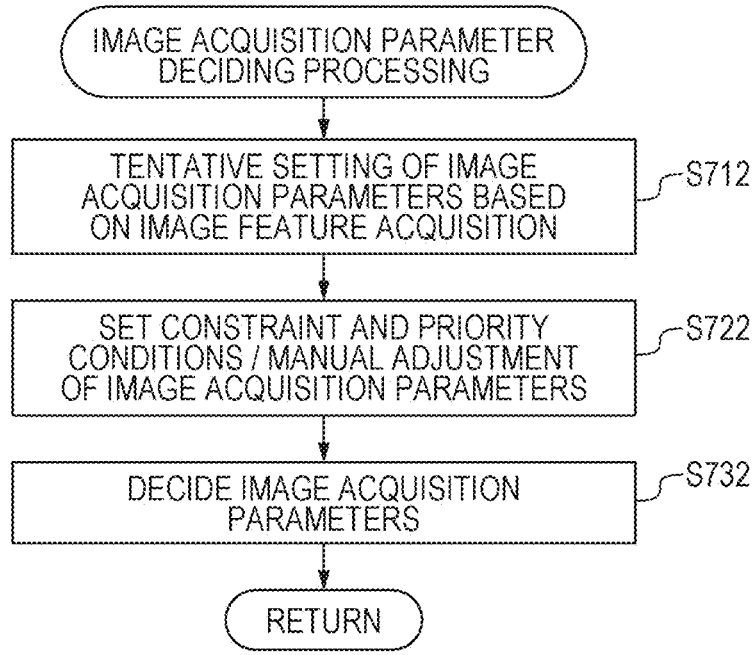
[Fig. 7D]
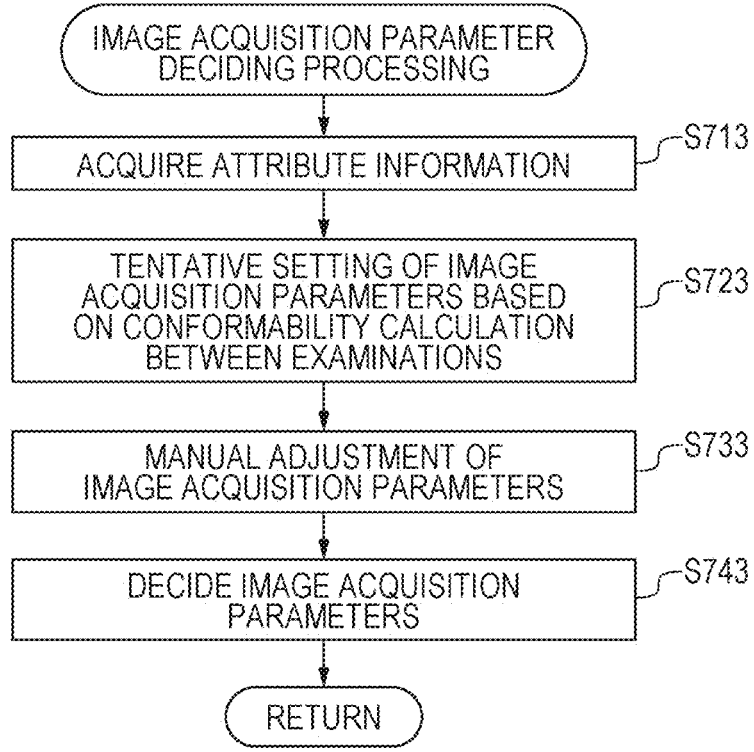

[Fig. 8A]
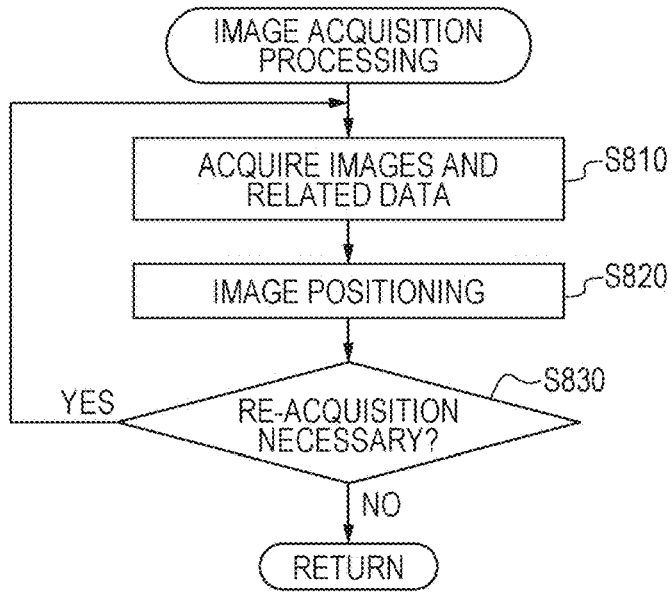
[Fig. 8B]
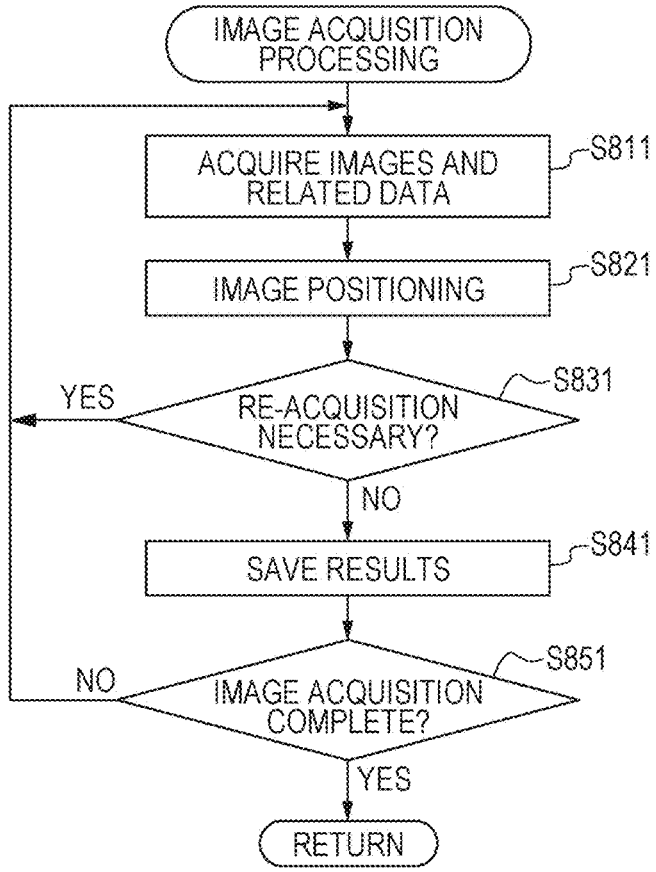

[Fig. 9]
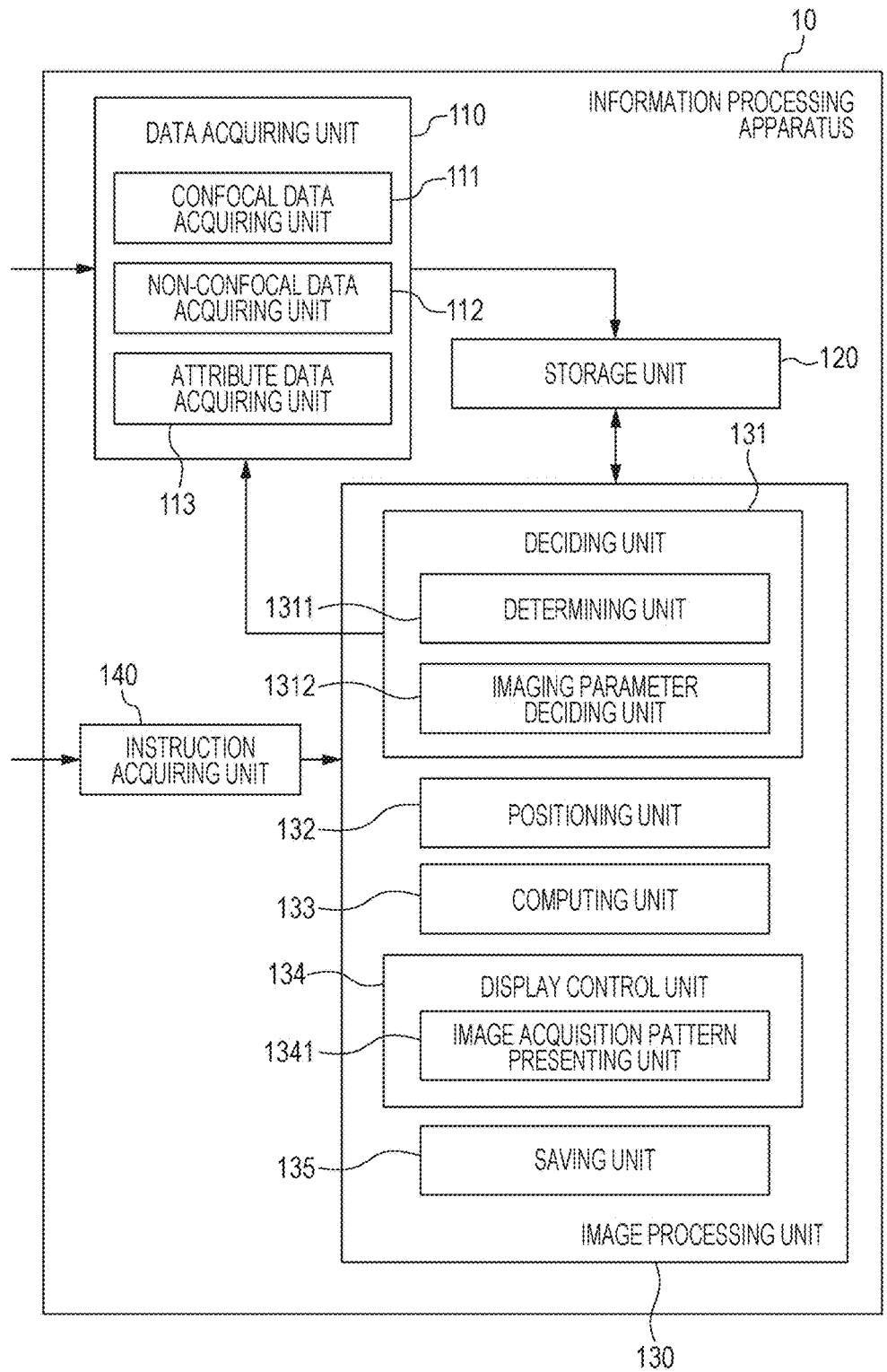

[Fig. 10]
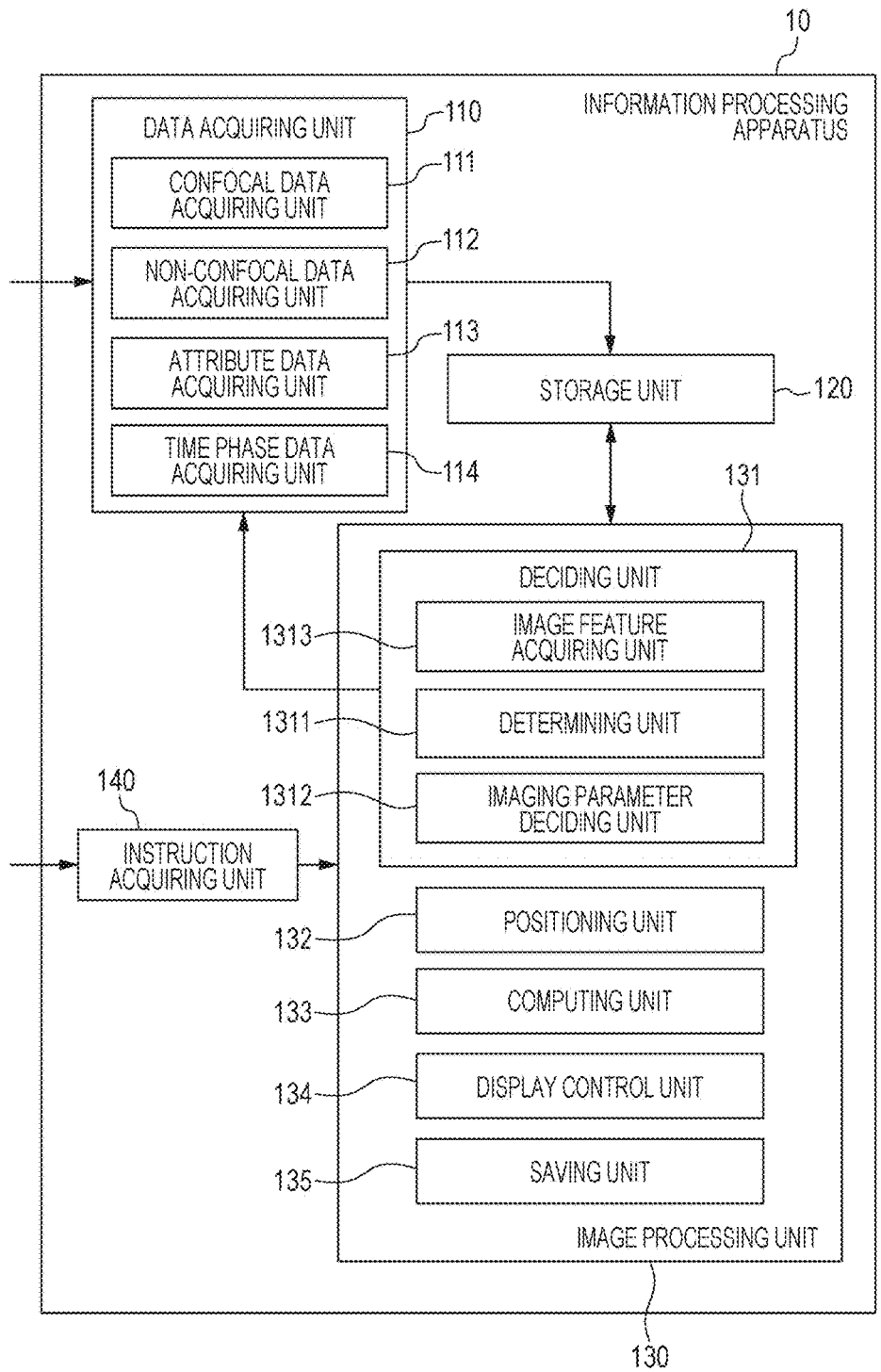

[Fig. 11]
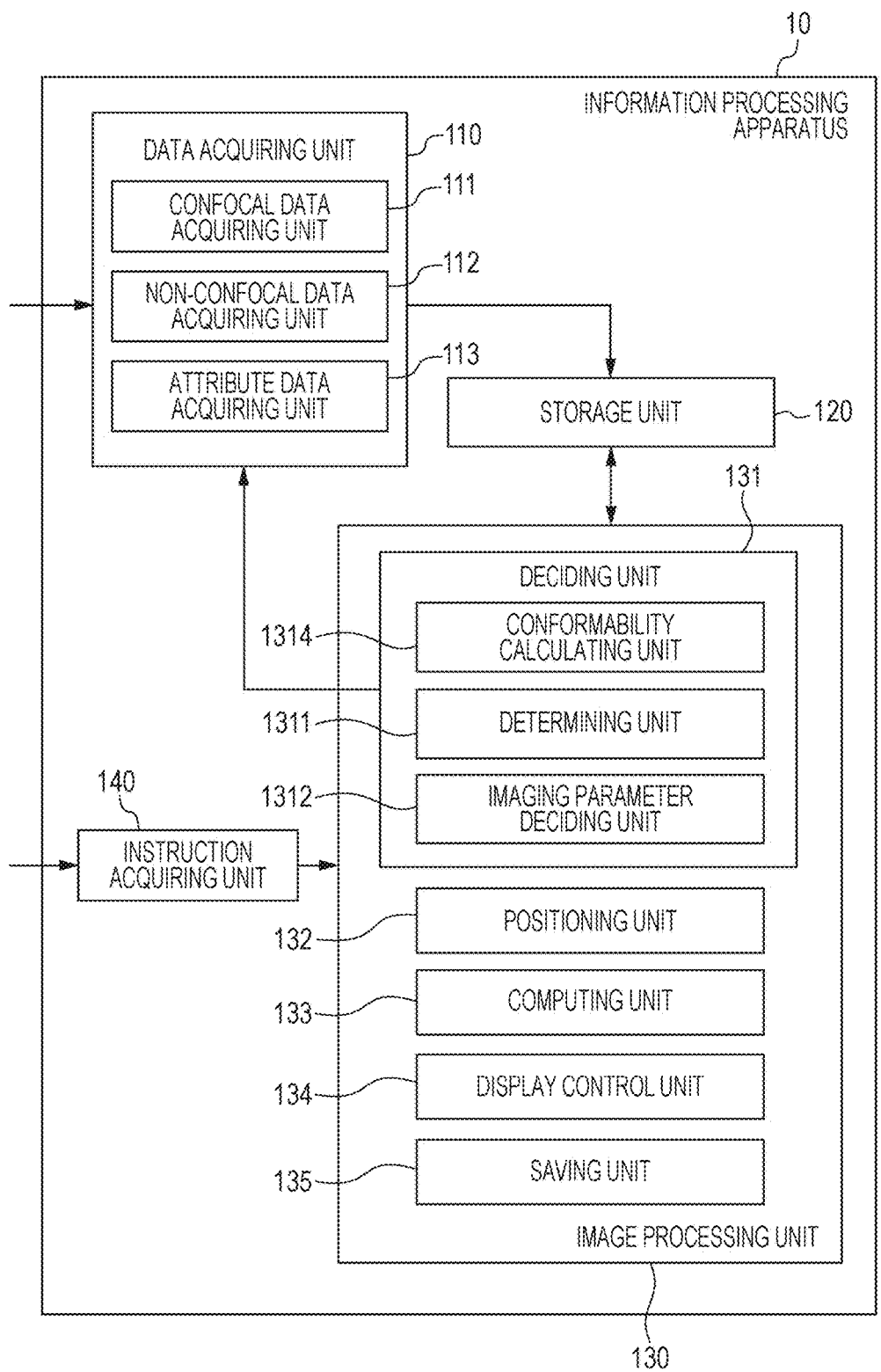

OPHTHALMOLOGIC IMAGING APPARATUS, OPERATION METHOD THEREOF, AND COMPUTER PROGRAM

TECHNICAL FIELD

The present invention relates to an ophthalmologic imaging apparatus used in ophthalmological diagnosis and treatment, an operation method thereof, and a computer program.

BACKGROUND ART

Examination of the eye is widely performed for early diagnosis and treatment of lifestyle diseases and diseases which are primary causes of loss of eyesight. The scanning laser ophthalmoscope (SLO), which is an ophthalmological apparatus that employs the principle of confocal laser scanning microscopy, performs raster scanning of a laser, which is measurement light, over the fundus, and acquires a high-resolution planar image from the intensity of returning light at high speed. Detecting only light that has passed through an aperture (pinhole) enables an image to be formed just using returning light of a particular depth position, and images with higher contrast than fundus cameras and the like can be acquired. An apparatus which images such a planar image will hereinafter be referred to as an SLO apparatus, and the planar image to as an SLO image.

In recent years, increased beam diameter of measurement light in SLO apparatuses has enabled acquisition of SLO images of the retina, with improved horizontal resolution. However, the increased beam diameter of the measurement light has led to a problem of deterioration the sound-to-noise (SIN) ratio and the resolution of the SLO image during acquisition of SLO images of the retina, due to aberration of the eye being examined. An adaptive optic SLO apparatus has been developed to solve this problem. The adaptive optic SLO apparatus has an adaptive optic system that measures aberration of the eye being examined in real time using a wavefront sensor, and corrects aberration occurring in the eye being examined with regard to the measurement light and the returning light thereof using a wavefront correction device. This enables SLO images with high horizontal resolution (high-magnification image) to be acquired.

Such a high horizontal resolution SLO image can be acquired as a moving image. In order to noninvasively observe hemodynamics, for example, retinal blood vessels are extracted from each frame, and the moving speed of blood cells through capillaries and so forth is measured. Also, in order to evaluate the relation with visual function using an SLO image, photoreceptors P are detected, and the density distribution and array of the photoreceptors P are calculated. FIG. 6B illustrates an example of a high horizontal resolution SLO image. The photoreceptors P, a low-luminance region Q corresponding to the position of capillaries, and a high-luminance region W corresponding to the position of a white blood cell, can be observed. In a case of observing photoreceptors P in the SLO image, the focus position is set nearby the outer layer of the retina (B5 in FIG. 6A) to take a SLO image such as in FIG. 6B. On the other hand, there are retinal blood vessels and capillaries that have branched running through the inner layers of the retina (B2 through B4 in FIG. 6A). Acquiring an adaptive optics SLO image with the focus position set in the inner layers of the retina enables the retinal blood vessel walls, which are fine structures relating to retinal blood vessels, to be directly observed.

However, confocal images taken of the inner layers of the retina have intense noise signals due to the influence of light reflecting from the nerve fiber layer, and there have been cases where observing blood vessel walls and detection of wall boundaries has been difficult. Accordingly, as of recent, techniques have come into use using observation of non-confocal images obtained by acquiring scattered light, by changing the diameter, shape, and position of a pinhole on the near side of the light receiving portion (NPL 1). Non-confocal images have a great depth of focus, so objects that have unevenness in the depth direction, such as blood vessels can be easily observed, and also noise is reduced since reflected light from the nerve fiber layer is not readily directly received. While observation of photoreceptors at the outer layers of the retina has primarily involved imaging confocal images of the outer segment of photoreceptors, it has been found that the unevenness of the inner segment of photoreceptors can be imaged in non-confocal images (NPL 2). Although a region where an initial lesion has damaged the outer segment but the inner segment has survived is imaged as a black defect area in confocal images (Dc5 in FIG. 6K), this can be observed as a region where high-luminance granular objects exist in non-confocal images (Dn5 in FIG. 6L). NPL 1 discloses technology for acquiring non-confocal images of retinal blood vessels using an adaptive optics SLO apparatus, while NPL 2 discloses technology for acquiring both confocal images and non-confocal images at the same time using an adaptive optics SLO apparatus. Further, technology for effectively taking tomographic images of the eye is disclosed in PTL 1.

CITATION LIST

Patent Literature

PTL 1: Japanese Patent Laid-Open No. 2010-35607

Non Patent Literature

NPL Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014

NPL 2: Scoles, Dubra et al.; "In vivo Imaging of Human Cone Photoreceptor Inner Segment", IOVS, Vol. 55, No. 7, pp. 4244-4251, 2014

SUMMARY OF INVENTION

Solution to Problem

Embodiments of an information processing apparatus according to the present invention and an operation method thereof have the following configurations, for example.

An ophthalmologic imaging apparatus that acquires a plurality of types of images of an eye including a confocal image and a non-confocal image of the eye, includes a deciding unit configured to decide conditions relating to acquisition of the plurality of types of images, for each type of the plurality of types of images, and a control unit configured to control the ophthalmologic imaging apparatus to acquire at lest one of the plurality of types of images, in accordance with the decided conditions.

An operation method of an ophthalmologic imaging apparatus that acquires a plurality of types of images of an eye including a confocal image and a non-confocal image of the eye includes a step of deciding conditions relating to acquisition of the plurality of types of images, for each type of the plurality of types of images, and a step of controlling the ophthalmologic imaging apparatus to acquire at lest one of the plurality of types of images, in accordance with the decided conditions.

Further features of the present invention will become apparent from the following description of exemplary embodiments with reference to the attached drawings.

BRIEF DESCRIPTION OF DRAWINGS

FIG. 1 is a block diagram illustrating a functional configuration example of an information processing apparatus according to a first embodiment of the present invention.

FIG. 2A is a block diagram illustrating a configuration example of a system including the information processing apparatus according to an embodiment of the present invention.

FIG. 2B is a block diagram illustrating a configuration example of a system including the information processing apparatus according to an embodiment.

FIG. 3A is a diagram for describing the overall configuration of an SLO image imaging apparatus according to an embodiment of the present invention.

FIG. 3B is a diagram for describing part of the configuration of the SLO image imaging apparatus in FIG. 3A.

FIG. 3C is a diagram for describing part of the configuration of the SLO image imaging apparatus in FIG. 3A.

FIG. 3D is a diagram for describing part of the configuration of the SLO image imaging apparatus in FIG. 3A.

FIG. 3E is a diagram for describing part of the configuration of the SLO image imaging apparatus in FIG. 3A.

FIG. 3F is a diagram for describing part of the configuration of the SLO image imaging apparatus in FIG. 3A.

FIG. 3G is a diagram for describing part of the configuration of the SLO image imaging apparatus in FIG. 3A.

FIG. 3H is a diagram for describing part of the configuration of the SLO image imaging apparatus in FIG. 3A.

FIG. 4 is a block diagram illustrating a hardware configuration example of a computer which has hardware equivalent to a storage unit and image processing unit and holds other units as software which is executed.

FIG. 5A is a flowchart of processing which the information processing apparatus according to an embodiment of the present invention executes.

FIG. 5B is a flowchart of processing which the information processing apparatus according to an embodiment of the present invention executes.

FIG. 6A is a diagram for describing image processing according to an embodiment of the present invention.

FIG. 6B is a diagram for describing image processing according to an embodiment of the present invention.

FIG. 6C is a diagram for describing image processing according to an embodiment of the present invention.

FIG. 6D is a diagram for describing image processing according to an embodiment of the present invention.

FIG. 6E is a diagram for describing image processing according to an embodiment of the present invention.

FIG. 6F is a diagram for describing image processing according to an embodiment of the present invention.

FIG. 6G is a diagram for describing image processing according to an embodiment of the present invention.

FIG. 6H is a diagram for describing image processing according to an embodiment of the present invention.

FIG. 6I is a diagram for describing image processing according to an embodiment of the present invention.

FIG. 6J is a diagram for describing image processing according to an embodiment of the present invention.

FIG. 6K is a diagram for describing image processing according to an embodiment of the present invention.

FIG. 6L is a diagram for describing image processing according to an embodiment of the present invention.

FIG. 7A is a flowchart illustrating the details of processing executed in S510 in the first embodiment.

FIG. 7B is a flowchart illustrating the details of processing executed in S511 in a second embodiment.

FIG. 7C is a flowchart illustrating the details of processing executed in S511 in a third embodiment.

FIG. 7D is a flowchart illustrating the details of processing executed in S511 in a fourth embodiment.

FIG. 8A is a flowchart illustrating the details of processing executed in S520 in the first embodiment.

FIG. 8B is a flowchart illustrating the details of processing executed in S521 in the second through fourth embodiments.

FIG. 9 is a block diagram illustrating a functional configuration example of an information processing apparatus according to the second embodiment of the present invention.

FIG. 10 is a block diagram illustrating a functional configuration example of an information processing apparatus according to the third embodiment of the present invention.

FIG. 11 is a block diagram illustrating a functional configuration example of an information processing apparatus according to the fourth embodiment of the present invention.

DESCRIPTION OF EMBODIMENTS

SLO apparatuses that acquire confocal images and non-confocal images generally acquire all types of images with the same imaging parameters. In doing so, there is a possibility that the amount of acquired data is larger than the data capacity that the central processing unit (CPU) can process in unit time. Accordingly, there is demand to efficiently use limited CPU resources to perform examination efficiently.

Accordingly, one aspect of an embodiment is an ophthalmologic imaging apparatus that acquires multiple types of images of an eye including at least one type of non-confocal image of the eye. An example of the ophthalmologic imaging apparatus is an SLO imaging apparatus 20 communicably connected with an information processing apparatus 10, illustrated in FIGS. 2A and 2B. The SLO imaging apparatus 20 in FIG. 2A and 2B may have the information processing apparatus 10 integrally built in. Also, one aspect of an embodiment is a control unit that controls the ophthalmologic imaging apparatus to acquire at least one of the plurality of types of images, by conditions relating to acquisition of the plurality of types of images. An example of the control unit is a data acquiring unit 110. The control unit does not have to be provided at the information processing apparatus 10, and may be configured as a central processing unit (CPU) or the like provided to the ophthalmologic imaging apparatus. Accordingly, multiple types of images of the eye including at least one type of non-confocal image can be efficiently acquired.

Another aspect of an embodiment is an ophthalmologic imaging apparatus that acquires multiple types of images of an eye including a confocal image and at least one type of non-confocal image of the eye. Another aspect of an embodiment includes a deciding unit that decides conditions relating to acquisition of the multiple types of images for each image type (an example is a deciding unit 131 in FIG.

1). Another aspect of an embodiment includes a control unit that controls the ophthalmologic imaging apparatus to acquire at least one of the plurality of types of images, by conditions that have been decided. Accordingly, multiple types of images of the eye including a confocal image and at least one type of non-confocal image of the eye can be efficiently acquired.

Another aspect of an embodiment preferably efficiently performs image processing acquisition upon having decided whether or not to acquire an image and a method of acquisition, in accordance with attributes of imaged images, and whether the images include anatomical features or lesion portions. That is to say, an apparatus that acquires multiple types of images with different light receiving methods performs acquisition image processing with priority on images which are more important with regard to observation and measurement necessitates acquisition of a great number of images more efficiently. Now, the technology described in NPL 1 discloses technology relating to an adaptive optics SLO apparatus that acquires multi-channel non-confocal images, but does not disclose a method to efficiently generate or measure a great number of types of non-confocal images. Although the technology described in NPL 2 acquires confocal images and non-confocal images at the same time, there is no disclosure of a method of efficiently generating or measuring confocal images and non-confocal images. Further, the technology in NPL 1 discloses deciding image acquisition parameters of tomographic images of the eye, based on lesion candidate regions acquired from a wide-angle image. However, an efficient acquisition method of multiple images including one or more types of non-confocal images is not disclosed.

Embodiments of an ophthalmologic imaging apparatus, an operation method thereof, and a computer program, according to the present invention, will be described below with reference to the attached drawings. It should be noted, though, that the present invention is not restricted to this description.

(First Embodiment: Deciding Different Acquisition Conditions by Specified Imaging Position)

An ophthalmologic imaging apparatus according to a first embodiment is configured to acquire confocal images and non-confocal images using image acquisition parameters decided for each image type beforehand, so that when an operator specifies a imaging position, images that are more crucial for observation and measurement have a greater data amount. Specifically, in a case of acquiring confocal images Dc and non-confocal images Dn (Dnr and Dnl) of photoreceptors of the eye, with the operator having specified the macular area as the imaging position, images are acquired as follows. That is to say, description will be made regarding an arrangement where confocal images Dcj and two types of non-confocal images Dnrk and Dnlk are the types of images taken at the parafovea, and the frame rate of the non-confocal images is lower than that of the confocal images. On the other hand, the type of images taken farther than 1.5 mm from the fovea is just confocal images Dcj, and the resolution is lower than at the parafovea.

Overall Configuration

FIG. 2A is a configuration diagrams of a system including the information processing apparatus 10 according to the present embodiment. The information processing apparatus 10 is connected to an SLO image imaging apparatus 20, which is an example of an ophthalmic imaging apparatus, and a data server 40, via a local area network (LAN) 30 including optical fiber, Universal Serial Bus (USB), IEEE 1394, or the like, as illustrated in FIG. 2A. The configuration of connection to these devices may be via an external network such as the Internet, or may be a configuration where the information processing apparatus 10 is directly connected to the SLO image imaging apparatus 20. Alternatively, the information processing apparatus 10 may be integrally built into an ophthalmic imaging apparatus.

The SLO image imaging apparatus 20 is an apparatus to image confocal images Dc and non-confocal images Dn, which are wide-angle images Dl and high-magnification images Dh of the eye. The SLO image imaging apparatus 20 transmits wide-angle images Dl, confocal images Dc, non-confocal images Dn, and information of fixation target positions Fl and Fcn used for imaging thereof, to the information processing apparatus 10 and the data server 40. In a case where these images are acquired at different imaging positions, this is expressed as Dli, Dcj, Dnk. That is to say, i and j are variables indicating the numbers for the imaging positions, where i=1, 2, . . . , imax, j=1, 2, . . . , jmax and k=1, 2, . . . , kmax. In a case of acquiring confocal images Dc and non-confocal images Dn at different magnifications, this is expressed like Dc1$m$, Dc2$o$, . . . (Dn1$m$, Dn2$o$, . . . ) in order from the highest-magnification image, with Dc1$m$ (Dn1$m$) denoting high-magnification confocal (non-confocal) images, and Dc2$o$, . . . (Dn2$o$, . . . ) denoting mid-magnification confocal images (non-confocal images).

The data server 40 holds the wide-angle images Dl, confocal images Dc, and non-confocal images Dn, of the examinee eye, imaging conditions data such as fixation target positions Fl and Fcn used for the imaging thereof, image features of the eye, and so forth. In the present invention, image features relating to the photoreceptors P, capillaries Q, and retinal blood vessel walls, are handled as image features of the eye. The wide-angle images Dl, confocal images Dc, and non-confocal images Dn output from the SLO image imaging apparatus 20, fixation target positions Fl and Fcn used for the imaging thereof, and image features of the eye output from the information processing apparatus 10, are saved in the server 40. Also, the wide-angle images Dl, confocal images Dc, and non-confocal images Dn, and image features of the eye, are transmitted to the information processing apparatus 10 in response to requests from the information processing apparatus 10.

Next, the functional configuration of the information processing apparatus 10 according to the present embodiment will be described with reference to FIG. 1. FIG. 1 is a block diagram illustrating the functional configuration of the information processing apparatus 10. The information processing apparatus 10 includes a data acquiring unit 110, a storage unit 120, an image processing unit 130, and an instruction acquiring unit 140. The data acquiring unit 110 includes a confocal data acquiring unit 111, a non-confocal data acquiring unit 112, and an attribute data acquiring unit 113. The image processing unit 130 includes a deciding unit 131, a positioning unit 132, a computing unit 133, a display control unit 134, and a saving unit 135. The deciding unit 131 further has a determining unit 1311 and a imaging parameter deciding unit 1312.

Now, the SLO imaging apparatus 20 that applies adaptive optics will be described with reference to FIGS. 3A and 3B. The SLO imaging apparatus 20 includes a superluminiscent diode (SLD) 201, a Shack-Hartman wavefront sensor 206, an adaptive optics system 204, beam splitters 202 and 203, an X-Y scanning mirror 205, a focus lens 209, a diaphragm 210, a photosensor 211, an image forming unit 212, and an output unit 213.

Light irradiated from the SLD 201 that is the light source is reflected at the fundus. Part of the reflected light is input to the Shack-Hartman wavefront sensor 206 via the second beam splitter 203, and the remaining reflected light is input to the photosensor 211 via the first beam splitter 202. Although the light source here services both as a light source for acquiring confocal images and a light source for acquiring non-confocal images, multiple light sources configured to emit different wavelengths may be used, or the like. The Shack-Hartman wavefront sensor 206 is a device to measure aberration of the eye, in which a lens eye 207 is connected to a charge-coupled device (CCD) 208. Upon input light being transmitted through the lens eye 207, bright point set appears on the CCD 208, and wave aberration is measured base on the positional gap of the projected bright points. The adaptive optics system 204 drives an aberration correction device (deformable mirror or spatial light phase modulator) to correct the aberration, based on the wave aberration measured by the Shack-Hartman wavefront sensor 206. The light subjected to aberration-correction passes through the focus lens 209 and diaphragm 210, and is received at the photosensor 211. The diaphragm 210 and photosensor 211 are examples of the aperture and photoreceptor according to the present invention. The aperture preferably is provided upstream of the photoreceptor and near to the photoreceptor. The scanning position on the fundus can be controlled by moving the X-Y scanning mirror 205, thereby acquiring data according to an imaging region and time (frame rate×frame count) that the operator has instructed. The data is transmitted to the image forming unit 212, where image distortion due to variation in scanning rate is corrected and luminance value correction is performed, thereby forming image data (moving image or still image). The output unit 213 outputs the image data formed by the image forming unit 212.

The configuration of the diaphragm 210 and photosensor 211 portion in FIG. 3A is optional, just as long as the SLO imaging apparatus 20 is configured to be able to acquire confocal images Dc and non-confocal images Dn. The present embodiment is configured using a light-shielding member 210-1 (FIGS. 3B and 3E) and photosensor 211-1, 211-2, and 211-3 (FIG. 3B). Regarding the returning light in FIG. 3B, part of the light that has entered the light-shielding member 210-1 disposed at the image forming plate is reflected and enters the photosensor 211-1. Now, the light-shielding member 210-1 will be described with reference to FIG. 3E. The light-shielding member 210-1 is formed of transmitting regions 210-1-2 and 210-1-3, a light-shielded region (omitted from illustration), and a reflecting region 210-1-1, so that the center is positioned on the center of the optical axis of the returning light. The light-shielding member 210-1 has an elliptic shape pattern so that when disposed obliquely as to the optical axis of the returning light, the shape appears to be circular when seen from the optical axis direction. The returning light divided at the light-shielding member 210-1 is input to the photosensor 211-1. The returning light that has passed through the transmitting regions 210-1-2 and 210-1-3 of the light-shielding member 210-1 is split by a prism 210-2 disposed at the image forming plane, and is input to photosensors 211-2 and 211-3, as illustrated in FIG. 3B. Voltage signals obtained at the photosensors are converted into digital values at an AD board within the image forming unit 212, thereby forming a two-dimensional image. The image based on light entering the photosensor 211-1 is a confocal image where focus has been made on a particular narrow range. Images based on light entering the photosensors 211-2 and 211-3 are non-confocal images where focus has been made on a broad range. The light-shielding member 210-1 is an example of an optical member that divides returning light from the eye which has been irradiated by light from the light source, into returning light passing through a confocal region and returning light passing through a non-confocal region. The transmitting regions 210-1-2 and 210-1-3 are examples of a non-confocal region, and non-confocal images are acquired based on the returning light passing through the non-confocal regions. The reflecting region 210-1-1 is an example of a confocal region, and confocal images are acquired based on the returning light passing through the confocal region.

The method for dividing non-confocal signals is not restricted to this, and a configuration may be made where non-confocal signals are divided into four and received, such as illustrated in FIG. 3F, for example. Also, the reception method of confocal signals and non-confocal signals is not restricted to this. For example, a mechanism is preferably had where the diameter and position of the diaphragm 210 (aperture) is changeable. In doing so, at least one of the diameter of the aperture and the position in the optical axis direction is configured so as to be adjustable, so as to receive as confocal signals as illustrated in FIG. 3C and to receive as non-confocal signals as illustrated in FIG. 3D. The diameter and movement amount of the aperture may be optionally adjusted. For example, FIG. 3C shows that the diameter of the aperture can be adjusted to around 1 Airy disc diameter (ADD), and FIG. 3D shows that the diameter of the aperture can be adjusted to around 10 ADD with a movement amount of around 6 ADD. Alternatively, a configuration may be made where multiple non-confocal signals are received at the same time, as in FIGS. 3G and 3H. There are two types of non-confocal signals in the present embodiment, so one will be denoted by Dnr referring to the R channel image, and the other will be denoted by Dnl referring to the L channel image. The notation "non-confocal image Dn" refers to both the R channel image Dnr and L channel image Dnl.

The SLO imaging apparatus 20 can also operate as a normal SLO apparatus, by increasing the scan angle of the scanning optical system in the configuration in FIG. 3A, and instructing so that the adaptive optics system 204 does not perform aberration correction, so as to acquire wide-angle images. Images which are lower magnification than the high-magnification images Dc and Dn, and have the lowest magnification of images acquired by the data acquiring unit 110 will be referred to as wide-angle images Dl (Dlc, Dln). Accordingly, a wide-angle image Dl may be an SLO image where adaptive optics has been applied, and cases of a simple SLO image are also included. Note that when distinguishing between confocal wide-angle images and non-confocal wide-angle images, these are denoted by Dlc and Dln. Note that in the present embodiment, images which have a relatively lower magnification that high-magnification images are collectively referred to as low-magnification images. Accordingly, wide-angle images and mid-magnification images are included in low-magnification images.

Next, the hardware configuration of the information processing apparatus 10 will be described with reference to FIG. 4. In FIG. 4, 301 denotes a central processing unit (CPU), 302 memory (random access memory (RAM)), 303 control memory (read-only memory (ROM)), 304 an external storage device, 305 a monitor, 306 a keyboard, 307 a mouse, and 308 an interface. Control programs for realizing the image processing functions according to the present embodiment, and data used at the time of the control programs being executed, are stored in the external storage device 304. The control programs and data are loaded to the RAM 302 via a bus 309 as appropriate under control of the CPU 301, executed by the CPU 301, and function as the units described below. The functions of the blocks making up the information processing apparatus 10 will be correlated with specific execution procedures of the information processing apparatus 10 illustrated in the flowchart in FIG. 5A.

Step 510: Deciding Image Acquisition Parameters

The image processing unit 130 acquires a preset value list 121 of imaging conditions from the storage unit 120. In the present embodiment, the operator specifies information relating to the acquisition position and focus position of images, via the instruction acquiring unit 140. The preset value list 121 for the imaging conditions include whether or not to acquire (i.e., acquisition necessity), for each type of image (confocal/R channel/L channel), and in a case of acquiring, Number of gradients
Field angle
Resolution
Frame rate
Number of seconds for acquisition as preset values for imaging conditions at each acquisition position and focus position. The determining unit 1311 determines whether or not to acquire each image type at the imaging position and focus position specified by the operator, based on the preset values. The imaging parameter deciding unit 1312 decides acquisition parameters for the image at the acquisition position and focus position the determining unit 1311 has determined to be necessary, using the preset values.

Next, the operator changes the individual image acquisition parameters that have been decided as necessary, either for this acquisition alone, or changes the preset values. If there is the changed image acquisition parameters and the new preset value parameter, the determining unit 1311 and imaging parameter deciding unit 1312 overwrite the parameter with the changed value or the new preset value, and decide the final image acquisition parameters. Specifics of image acquisition parameter deciding processing will be decided in detail with reference to S710 through S730.

Although description has been made regarding a case where preset values are prepared for each acquisition position or focus position of an image, the present invention is not restricted to this. For example, a case where images are acquired based on acquisition necessity and acquisition parameters for each image type, uniformly stipulated unrelated to imaging position and focus position, is also included in the present invention. The operator changing individual image acquisition parameters and changing preset values is not indispensable to the present invention, and a case where the image acquisition parameters and preset values are not changed is also included in the present invention.

Step 520: Image Acquisition

The data acquiring unit 110 acquires images based on the image acquisition parameters decided in S510. In the present embodiment, all types of images are not acquired with the same image acquisition parameters. Images which are relatively low in importance in observation and measurement are set to have a lower number of frames or resolution, thereby efficiently acquiring images. Next, the positioning unit 132 performs inter-frame positioning and tiling processing on the acquired images. Further, the image processing unit 130 determines the necessity to re-acquire images based on luminance value, image quality, etc., of acquired images. Specifics of image acquiring processing will be described in detail in S810 through S830.

Step 530: Display

The computing unit 133 performs computation among inter-frame-positioned images, and generates an image. In the present embodiment, a Split Detector image is generated using an R-channel image Dark and an L-channel image $Dn1k$. Note that a Split Detector image is a type of a differential image using non-confocal images generated by computing ((pixel value of L-channel image−pixel value of R-channel image)/(pixel value of R-channel image+pixel value of L-channel image)). The display control unit 134 displays the acquired image on the monitor 305. A composited image of confocal image Dcj and Split Detector images Dnsk is subjected to composited display on the monitor 305 using positioning parameters decided in S820. The type of image to be displayed is switched using a graphical user interface (GUI) that has been prepared for this purpose. Although radio buttons are used for switching in the present embodiment, any GUI arrangement may be used for the switching. The types of images to be switched are the two types of confocal image Dc and Split Detector image Dns.

Step 540: Saving Results

The saving unit 135 correlates the examination date and information identifying the examinee eye with the images acquired in S520, the image generated in S530, and the positioning parameters, and transmits this to the data server 40.

Step 550: Determining Whether or not Image Acquisition is Complete

The instruction acquiring unit 140 externally acquires an instruction regarding whether or not to end acquisition processing of the wide-angle images Dl, high-magnification confocal images Dcj, and high-magnification non-confocal images Dnk, by the information processing apparatus 10. In a case of having obtained an instruction to end image acquisition processing, the processing ends. In a case of having obtained an instruction to continue image acquisition, the flow returns to S510, and the next image acquisition parameter is decided. This instruction is input by an operator by way of the keyboard 306 or mouse 307, for example.

Next, the processing executed in S510 will be described in detail with reference to the flowchart in FIG. 7A.

Step 710: Acquiring Preset Values of Image Acquisition Parameters

The image processing unit 130 acquires the preset value list 121 of imaging conditions from the storage unit 120. The determining unit 1311 determines the acquisition necessity for each image type, with regard to the imaging position and focus position that the operator has specified, based on the acquired preset values. The imaging parameter deciding unit 1312 decides the acquisition parameters for an image of the acquisition position and focus position regarding which necessity of acquisition has been determined, using the preset values listed in the preset value list 121.

Description will be made in the present embodiment regarding a case where the operator has specified a focus position of the outer layer of the retina (neuroepithelial layer) at a position 0.5 mm toward the nasal side from the fovea and 0.5 mm on the superior side. The preset value list 121 as set therein preset values (acquisition necessity, number of gradients, field angle, resolution, frame rate, number of seconds for acquisition)=(necessary, 16 bits, 3°×3°, 800 pixels×800 pixels, 32 fps, 3 seconds), as preset values relating to acquisition of confocal images in a case where an acquisition position within a radius of 1.5 mm from the fovea of the macular area and a focus depth of the neuroepithelial layer has peen specified. The preset values relating to acquisition of non-confocal images is (acquisition necessity, number of gradients, field angle, resolution, frame rate, number of seconds for acquisition)=(necessary, 16 bits, 3°×3°, 800 pixels×800 pixels, 16 fps, 3 seconds). The reason that the number of frames is fewer in the Split Detector image generated using non-confocal images is that this is an image to be observed in a supplementary manner, so not as many frames are necessary for use in compositing as compared to the confocal images.

The preset value list 121 may also include preset values for imaging positions and focus positions. For example, the density of cone cells is low at an acquisition position farther than a radius of 1.5 mm from the fovea, so cones can be observed even with a lower resolution. Accordingly, the preset value for acquiring confocal images is (acquisition necessity, number of gradients, field angle, resolution, frame rate, number of seconds for acquisition)=(necessary, 16 bits, 3°×3°, 400 pixels×400 pixels, 32 fps, 3 seconds). The preset values relating to acquisition of non-confocal images is (acquisition necessity, number of gradients, field angle, resolution, frame rate, number of seconds for acquisition)= (necessary, 16 bits, 3°×3°, 400 pixels×400 pixels, 16 fps, 3 seconds). Alternatively, in a case of imaging retinal blood vessel walls at the parafovea, the focus position is set to the inner layer of the retina. At the inner layers of the retina, there are intense noise signals due to light reflecting from the nerve fiber layer that is nearby the retinal blood vessels, so confocal images that have a small focal depth are not used for observing fine structures like retinal blood vessel walls, and non-confocal images that have a large focal depth are used for observation.

In a case of selecting only frames corresponding to a particular cardiac cycle to eliminate the influence of the heartbeat, and generate a composite image, a greater number of frames is necessary. Accordingly, the number of seconds of imaging is set longer in a case where the focus position is the outer layer of the retina. The preset value for acquiring confocal images in this case thus is (acquisition necessity, number of gradients, field angle, resolution, frame rate, number of seconds for acquisition)=(unnecessary). The preset values relating to acquisition of non-confocal images is (acquisition necessity, number of gradients, field angle, resolution, frame rate, number of seconds for acquisition)= (necessary, 16 bits, 3°×3°, 400 pixels×400 pixels, 32 fps, 4 seconds).

Preset values can be specified for wide-angle images in the same way. For example, in a case where the center of the acquisition position is set to the fovea and the focus position is set to the neuroepithelial layer, the preset values relating to acquisition of confocal wide-angle image Dlc is (acquisition necessity, number of gradients, field angle, resolution, frame rate, number of seconds for acquisition)=(necessary, 16 bits, 24°×18°, 800 pixels×600 pixels, 16 fps, 2 seconds). The preset values relating to acquisition of non-confocal wide-angle images Dln is (acquisition necessity, number of gradients, field angle, resolution, frame rate, number of seconds for acquisition)=(unnecessary).

In a case where non-confocal wide-angle images Dln are not acquired, positioning of wide-angle images and high-magnification images is performed such that positioning parameters decided between the non-confocal wide-angle images Dln and confocal high-magnification images Dc are also used for positioning of the confocal wide-angle images\ Dlc and non-confocal high-magnification images Dnk.

Step 720: Changing Preset values of Image Acquisition Parameters

Next, the operator changes the preset values of the image acquisition parameters that have been acquired in S710 as necessary, either for the acquisition parameters decided for this image of this acquisition alone, or changes the preset values. Any user interface may be used for changing the image acquisition parameters. In the present embodiment, the mouse 307 us used to change the image acquisition parameters values displayed as a slider on the monitor 305. This is not restrictive, and the changed values of the image acquisition parameters may be input from the keyboard 306 to an edit box of a combo box, for example, or the mouse 307 may be used to select changed values from a list box of combo box. In the present embodiment, none of the image acquisition parameters are changed, and the preset values obtained in S710 are used as they are.

Step 730: Deciding Image Acquisition Parameters

In a case where a changed value or new preset value is specified in S720, the determining unit 1311 and imaging parameter deciding unit 1312 overwrite with the changed value or the new preset value, and decide the final image acquisition parameters. In the case of the present embodiment, a focus position of the neuroepithelial layer at a position 0.5 mm toward the nasal side from the fovea and 0.5 mm on the superior side has been specified as the acquisition position of high-magnification images, and no change was made in S720, so the determining unit 1311 determines that the wide-angle image Dlc, confocal image Dc, and non-confocal images Dnr and Dnl need to be acquired. On the other hand, the imaging parameter deciding unit 1312 decides the image acquisition parameters for acquiring the confocal high-magnification image Dc to be (acquisition necessity, number of gradients, field angle, resolution, frame rate, number of seconds for acquisition)=(necessary, 16 bits, 3°×3°, 800 pixels×800 pixels, 32 fps, 3 seconds). The image acquisition parameters relating to acquisition of non-confocal high-magnification images Dnr and Dnl is decided to be (acquisition necessity, number of gradients, field angle, resolution, frame rate, number of seconds for acquisition)= (necessary, 16 bits, 3°×3°, 800 pixels×800 pixels, 16 fps, 3 seconds).

As for wide-angle images, the determining unit 1311 decides that acquisition of e confocal image Dlc is necessary, and the imaging parameter deciding unit 1312 decides the image acquisition parameters for acquiring the confocal wide-angle image Dlc to be (number of gradients, field angle, resolution, frame rate, number of seconds for acquisition)=(16 bits, 24°×18°, 800 pixels×600 pixels, 16 fps, 2 seconds) as final parameters.

The processing performed in S520 will now be described in detail with reference to the flowchart in FIG. 8A.

Step 810: Acquiring Images and Related Data

The data acquiring unit 110 requests the SLO imaging apparatus 20 to acquire wide-angle image Dlc and high-magnification images (confocal image Dc and non-confocal images Dnr and Dnl) based on the image acquisition parameters decided in S730. Acquisition of attribute data and fixation target positions Fl and Fcn corresponding to these images is also requested. In the present embodiment, the operator specifies a focus position of the neuroepithelial layer at a position 0.5 mm toward the nasal side from the fovea and 0.5 mm on the superior side for high-magnification images. The operator also specifies a focus position of the neuroepithelial layer at the center of the fovea. Now, the data acquiring unit 110 also functions as a control unit that controls the ophthalmologic imaging apparatus based on conditions relating to image acquisition. The control unit does not have to be provided to the information processing apparatus 10, and may be configured as a CPU or the like provided in the ophthalmologic imaging apparatus.

In accordance with the image acquisition parameters decided in S730, the data acquiring unit 110 requests acquisition of the confocal high-magnification image Dc at (acquisition necessity, number of gradients, field angle, resolution, frame rate, number of seconds for acquisition)= (necessary, 16 bits, 3°×3°, 800 pixels×800 pixels, 32 fps, 3 seconds). The acquisition of non-confocal high-magnification images Dnr and Dnl is requested at (acquisition necessity, number of gradients, field angle, resolution, frame rate, number of seconds for acquisition)=(necessary, 16 bits, 3°×3°, 800 pixels×800 pixels, 16 fps, 3 seconds).

The data acquiring unit 110 also requests acquisition of the confocal wide-angle image Dlc to be (number of gradients, field angle, resolution, frame rate, number of seconds for acquisition)=(16 bits, 24°×18°, 800 pixels×600 pixels, 16 fps, 2 seconds).

The SLO imaging apparatus 20 acquires and transmits the wide-angle image Dlc, confocal image Dc, non-confocal images Dnr and Dnl, corresponding attribute data, and fixation target positions Fl and Fcn in accordance with the acquisition request. The data acquiring unit 110 receives the wide-angle image Dlc, confocal image Dc, non-confocal images Dnr and Dnl, corresponding attribute data, and fixation target positions Fl and Fcn from the SLO imaging apparatus 20 via the LAN 30, and stores in the storage unit 120.

Step 820: Positioning Images

The positioning unit 132 performs positioning of the images acquired in S810. First, the positioning unit 132 performs inter-frame positioning of wide-angle image Dlc and confocal image Dc, and applies inter-frame positioning parameter values decided at the confocal image Dc to the non-confocal images Dlr and Dll as well. Specific frame positioning methods include the following.

i) The positioning unit 132 sets a reference frame to serve as a reference for positioning. In the present embodiment, the frame with the smallest frame No. is the reference frame. Note that the frame setting method is not restricted to this, and any setting method may be used.

ii) The positioning unit 132 performs general inter-frame correlation (rough positioning). Although any positioning technique may be used, the present embodiment performs rough positioning using a correlation coefficient as an inter-image similarity evaluation function, and Affine transform as a coordinate conversion technique.

iii) The positioning unit 132 performs fine positioning based on the data of the correspondence relation in the general position among the frames.

In the present embodiment, moving images that have been subjected to the rough positioning obtained in ii) are then subjected to inter-frame fine positioning, using free form deformation (FFD), which is a type of a non-rigid positioning technique. Note that the fine positioning technique is not restricted to this, and any positioning technique may be used.

After image generation, the positioning unit 132 positions wide-angle image Dlc and high-magnification image Dcj, and finds the relative position of Dcj on Dlc. The positioning unit 132 acquires the fixation target position Fen used at the time of imaging the high-magnification confocal images Dcj from the storage unit 120, to use as the initial point for searching for positioning parameters for the positioning of the wide-angle image Dlc and confocal image Dcj. The positioning of the wide-angle image Dlc and high-magnification confocal image Dcj is performed while changing combinations of the parameter values. The combination of positioning parameter values where the similarity between the wide-angle image Dlc and high-magnification confocal image Dcj is highest is decided to be the relative position of the confocal image Dcj as to the wide-angle image Dlc. Note that the positioning technique is not restricted to this, and any positioning technique may be used.

Also, in a case where a mid-magnification image has been acquired in S510, positioning is performed from images with lower magnification in order. For example, in a case where a high-magnification confocal image Dc1$m$ and a mid-magnification confocal image Dc2$o$ have been acquired, first, the wide-angle image Dlc and the mid-magnification image Dc2$o$ are positioned, and next, the mid-magnification image Dc2$o$ and the high-magnification image Dc1$m$ are positioned. Further, image tiling parameter values decided regarding the wide-angle confocal image Dlc and confocal image Dcj are applied to tiling of the wide-angle confocal image Dlc and non-confocal high-magnification images (Dnrk or Dnlk) as well. The relative positions of the high-magnification non-confocal images Dnrk and Dnlk, on the wide-angle confocal image Die are each decided.

Step 830: Determining Whether or not Re-acquisition is Necessary

The image processing unit 130 determines the necessity of re-acquisition of an image. First, if any of the frames of the moving image that has been acquired fall under a) Translation movement amount of moving image as to reference frame is equal to threshold Ttr or more b) Average luminance value of the frames is smaller than threshold Ti c) S/N ratio of the frames is smaller than threshold Tsn that frame is determined to be an exemption frame.

When viewing as a moving image, it is desirable that the image can be observed as long as possible without an exemption frame occurring, and in a case of generating a composited image, a certain number or more of images that can be composited are necessary. Accordingly, in the present embodiment, in a case where the maximum value of intervals between occurrence of exemption frames in a moving image is smaller than threshold Te or the total number of normal frames is smaller than threshold Ts, the image processing unit 130 determines that this image needs to be re-acquired. In a case where the image processing unit 130 determines that re-acquiring of the image is necessary, the image processing unit 130 requests the data acquiring unit 110 to re-acquire the image, and the flow advances to S510. On the other hand, re-acquiring of the image is determined to be unnecessary, the image acquisition processing is ended and the flow advances to S530. The method of determination of whether re-acquiring the image is necessary is not restricted to this, and any known determination method may be used. According to the configuration described above, when the operator instructs a imaging position, the information processing apparatus 10 acquires confocal images and non-confocal images using the image acquisition parameters decided for each image type, beforehand such that images that are more crucial for observation and measurement have a greater data amount. Accordingly, multiple types of images of the eye that are crucial for observation and analysis can be efficiently acquired.

Although the conditions relating to acquisition of the multiple types of images is decided beforehand for each type of the multiple types of images in the present embodiment, a configuration may be made where the conditions relating to acquisition for each type of the multiple types of images can be changed by user specification (e.g., selecting conditions relating to acquisition). Also, different conditions relating to acquisition for each type of the multiple types of images are preferably decided for each type of the multiple types of images. For example, conditions may be decided where confocal images are given priority over non-confocal images, with the non-confocal images not being acquired. Conversely, conditions may be decided where non-confocal images are given priority over confocal images, with the confocal images not being acquired. Also conditions of not acquiring images may be decided. Also, the decision of conditions relating to acquisition preferably includes decision of whether or not to acquire images. The conditions relating to acquisition are preferably decided in accordance with the imaging position in the multiple types of images (e.g., photoreceptors and blood vessels). For example, the conditions relating to acquisition are preferably decided so that the relationship in magnitude of the number of frames acquired for confocal images (example of data amount) and the number of frames acquired for non-confocal images differs depending on the imaging position. In a case where the imaging position is photoreceptors at this time, confocal images are more suitable than non-confocal images, so a greater number of frames of confocal images is preferably acquired. On the other hand, in a case where the imaging position is blood vessels, non-confocal images are more suitable than confocal images, so fewer frames of confocal images are preferably acquired. The above-described embodiment is applicable in the following embodiments as well.

(Second Embodiment: Deciding Conditions for Acquisition of Images Corresponding to an Image Acquisition Pattern Selected by Operator)

The information processing apparatus according to a second embodiment performs the following processing on images taken by a SLO apparatus that acquires confocal images and non-confocal images at the same time. The operator decides acquisition conditions for the images by selecting from basic patterns registered beforehand regarding multiple types of high-magnification image acquisition parameters at multiple locations. Specifically, in a case where there are provided image acquisition patterns indicated by Pr1 and Pr2 in FIG. 6I using an SLO apparatus such as illustrated in FIGS. 3A and 3B that acquires confocal images Dcj and non-confocal images Dnk at the same time, the operator decides the image acquisition parameters by selecting Pr1. Description will be made regarding a case where the preset values of the image acquisition parameters are decided beforehand for each image type at each acquisition position in the image acquisition pattern, and the operator adjusts image acquisition parameters at each imaging position as necessary. The configuration of apparatuses connected to the information processing apparatus 10 according to the present embodiment is the same as in the first embodiment, so description will be omitted.

Next, FIG. 9 illustrates a functional block diagram of the information processing apparatus 10 according to the present embodiment. This configuration differs from that in the first embodiment in that the storage unit 120 does not have the preset value list 121 of the imaging conditions, and instead the display control unit 134 has an image acquisition pattern presenting unit 1341. The image processing flow according to the present embodiment is as illustrated in FIG. 5B. The processing of the present embodiment is described below.

Step 511: Deciding Image Acquisition Parameters (1)

The display control unit 134 displays information relating to registered image acquisition patterns on the monitor 305. The image processing unit 130 acquires image preset values of acquisition parameters corresponding to an image acquisition pattern that the operator has selected via the instruction acquiring unit 140. In a case where the operator has specified constraint conditions (upper limit of total imaging time, etc.) or priority conditions (angle or imaging position to be give priority, etc.), the determining unit 1311 and imaging parameter deciding unit 1312 change the images that are the object of acquisitions, and the image acquisition parameters, to satisfy the constraint conditions and priority conditions. The image processing unit 130 also acquires individual image acquisition parameter values which the operator has specified as necessary, via the instruction acquiring unit 140. The determining unit 1311 determines final images that are the object of acquisition, based on preset values, constraint conditions, priority conditions, and individually specified parameter values, and the imaging parameter deciding unit 1312 decides the final image acquisition parameters. Specifics of the image acquisition parameter deciding processing will be described in detail in S711, S721, and S731. Image acquisition parameter deciding processing for wide-angle images is the same as in the first embodiment, so detailed description will be omitted.

Step 521: Acquiring Images (1)

The data acquiring unit 110 acquires images based on the image acquisition parameters decided in S511. Specifics of the image acquisition processing will be described in detail in S811, S821, S831, S841, and S851. Image acquisition parameter deciding processing for wide-angle images is the same as in the first embodiment, so detailed description will be omitted.

Step 531: Display (1)

The computing unit 133 performs computation among inter-frame-positioned images, and generates an image. The display control unit 134 displays the image acquired in S521 and the image generated in this step on the monitor 305.

Step 541: Determining Whether or not to End

The instruction acquiring unit 140 obtains an external instruction regarding whether or not to end the processing of the information processing apparatus 10 relating to wide-angle images Dl, high-magnification confocal images Dcj, and high-magnification non-confocal images Dnk. The instruction is input by the operator through the keyboard 306 or mouse 307. In a case of having obtained an instruction to end processing, the processing ends. On the other hand, in a case where an instruction is obtained to continue processing, the flow returns to S511, and processing is performed on the next examinee eye (or re-processing on the same examinee eye).

Next, the processing performed in S511 will be described in detail with reference to the flowchart in FIG. 7B.

Step 711: Selecting Image Acquisition Pattern

The display control unit 134 displays information relating to registered image acquisition patterns on the monitor 305. The image processing unit 130 obtains preset values of image acquisition parameters corresponding to the image acquisition pattern that the user has selected via the instruction acquiring unit 140.

Assumption will be made in the present embodiment that are provided image acquisition patterns indicated by Pr1 and Pr2 in FIG. 6I, and the operator selects Pr1. The closer to the center of the fovea, the higher the density of photoreceptors is, and the relationship with vision is high, so the closer the imaging positions of the images are to the fovea, the more crucial the images are regarding observation, and finer images are needed. Primarily confocal images are observed when observing photoreceptors, and non-confocal images such as Split Detector images are observed in a supplementary manner. Accordingly, in the image acquisition pattern Pr1, settings are made such that the closer to the fovea both confocal images and non-confocal images are, the finer images are acquired with more frames, and with regard to image type, confocal images are acquired with a higher number of gradations, thereby multiple types of images crucial for observation can be effectively acquired. Specifically, of the images (Dc1 through Dc9, Dnr1 through Dnr9, and Dnl1 through Dnl9) in Pr1, the following image acquisition parameters are set as preset values regarding images (Dc5, Dnr5, and Dnl5) since the acquisition position is the fovea, and these are decided as tentative image acquisition parameters. The parameters are tentatively set for the confocal high-magnification image Dc5 to be (number of gradients, field angle, resolution, frame rate, number of seconds for acquisition)=(16 bits, 1.5°×1.5°, 800 pixels×800 pixels, 32 fps, 2 seconds). The parameters are tentatively set for the non-confocal high-magnification images Dnr5 and Drl5 to be (number of gradients, field angle, resolution, frame rate, number of seconds for acquisition)=(8 bits, 1.5°×1.5°, 800 pixels×800 pixels, 32 fps, 2 seconds).

Also, for the images (Dc1 through Dc4 and Dc6 through Dc9, Dnr1 through Dnr4 and Dnr6 through Dnr9, and Dnl1 through Dnl4 and Drl6 through Drl9) that are somewhat on the outer side from the fovea, the following image acquisition parameters are set as preset values and these are decided as tentative image acquisition parameters. The parameters are tentatively set for the confocal high-magnification images Dc1 through Dc4 and Dc6 through Dc9 to be (number of gradients, field angle, resolution, frame rate, number of seconds for acquisition)=(16 bits, 1.5°×1.5°, 400 pixels×400 pixels, 16 fps, 2 seconds). The parameters are tentatively set for the non-confocal high-magnification images Dnr1 through Dnr4 and Dnr6 through Dnr9, and Dnl1 through Dn14 and Dnl6 through Dnl9, to be (number of gradients, field angle, resolution, frame rate, number of seconds for acquisition)=(8 bits, 1.5°×1.5°, 400 pixels×400 pixels, 16 fps, 2 seconds).

Step 721: Setting Constraint and Priority Conditions

In a case where the operator has specified constraint conditions (upper limit of total imaging time, etc.) or priority conditions (angle or imaging position to be give priority, etc.), the determining unit 1311 and imaging parameter deciding unit 1312 change the images that are the object of acquisitions, and the image acquisition parameters, to satisfy the constraint conditions and priority conditions. The image processing unit 130 also acquires individual image acquisition parameter values which the operator has specified as necessary, via the instruction acquiring unit 140.

Description will be made in the present embodiment regarding a case where the operator has set the upper limit to the total imaging time to 10 seconds, as constraint conditions, and has made settings to give priority to holding imaging parameters for subfoveal images. In S711, the total acquisition time of the images was a total of 18 seconds at nine locations, but instructions are given here to hold subfoveal image acquisition parameters as much as possible while keeping the upper limit of the total amount of time to 10 seconds. The determining unit 1311 and imaging parameter deciding unit 1312 change the images to be acquired and the image acquisition parameters to satisfy the constraint conditions and priority conditions. That is to say, the determining unit 1311 determines that acquisition of images at all positions and of all types is necessary, and the imaging parameter deciding unit 1312 decides to change the acquisition time of confocal images and of the non-confocal images in the perimeter of the fovea to be changed to 1 second, while the subfoveal image acquisition parameters are maintained. Accordingly, the acquisition parameters of the subfoveal confocal images and non-confocal images crucial for observation are kept maintained, while the total image acquisition time is shortened to (1 location×2 seconds)+(8 locations×1 second)=10 seconds. In a case where the number of images to be imaged is excessively large for the total imaging time specified as the constraint conditions, the determining unit 1311 determines not to acquire some images with low priority, and the imaging parameter deciding unit 1312 decides the image acquisition parameters to satisfy the constraint conditions.

A case where the image processing unit 130 acquires, via the instruction acquiring unit 140, acquisition necessity acquisition parameter values for individual images that the operator has changed as necessary, the image acquisition parameters tentatively decided in S711 are overwritten, and final image acquisition parameters are decided, is also included in the present invention. Also, generally, the earlier in the order of acquisition an image is acquired, the easier it is to acquire a high-quality image, since the fatigue of the subject is small, so the order of acquiring images may also be included as an image acquisition parameter. In this case, the order of acquiring images is also included in priority conditions. For example, in a case where priority is high for subfoveal images, the subfoveal images Dc5, Dnr5, and Dnl5 are acquired first, after which the parafoveal images Dc1 (and Dnr1 and Dnl1) through Dc4 (and Dnr4 and Dnl4), and Dc6 (and Dnr6 and Dnl6) through Dc9 (and Dnr9 and Dnl9) are acquired.

Step 731: Deciding Image Acquisition Parameters

The determining unit 1311 determines images that are the object of acquisition based on the following information, and the imaging parameter deciding unit 1312 decides the image acquisition parameters.

Preset values of image acquisition parameters corresponding to the image acquisition pattern selected by the operator in S711

Constraint conditions and priority conditions the operator instructed as necessary in S721

Individual image acquisition parameters values the operator has changed as necessary in S721

In the present embodiment, the determining unit 1311 determines all images of the images (Dc1 through Dc9, Dnr1 through Dnr9, and Dnl1 through Dnl9) in the image acquisition pattern Pr1 in FIG. 6I to be necessary to acquire. Further, the imaging parameter deciding unit 1312 decides, for the subfoveal confocal high-magnification image Dc5 (number of gradients, field angle, resolution, frame rate, number of seconds for acquisition)=(16 bits, 1.5°×1.5°, 800 pixels×800 pixels, 32 fps, 2 seconds). For the non-confocal high-magnification images Dnr5 and Dnl5, (number of gradients, field angle, resolution, frame rate, number of seconds for acquisition)=(8 bits, 1.5°×1.5°, 800 pixels×800 pixels, 32 fps, 2 seconds) are decided.

Also, of the images of Pr1 that are somewhat on the outer side from the fovea, the confocal high-magnification images Dc1 through Dc4 and Dc6 through Dc9 are decided to be (number of gradients, field angle, resolution, frame rate, number of seconds for acquisition)=(16 bits, 1.5°×1.5°, 400 pixels×400 pixels, 16 fps, 2 seconds). The non-confocal high-magnification images Dart through Dnr4 and Dnr6 through Dnr9, and Dnl1 through Dnl4 and Dnl6 through Dnl9, are decided to be (number of gradients, field angle, resolution, frame rate, number of seconds for acquisition) =(8 bits, 1.5°×1.5°, 400 pixels×400 pixels, 16 fps, 2 seconds).

Next, the processing performed in S521 will be described in detail with reference to the flowchart in FIG. 8B.

Step 811: Acquiring Images and Related Data (1)

The data acquiring unit 110 acquires images based on the image acquisition parameters decided in S511. Detailed procedures of image acquisition are the same as in S810 in the first embodiment, so detailed will be omitted.

Step 821: Positioning Images (1)

The positioning unit 132 performs positioning of image s acquired in S811. Detailed procedures of inter-frame positioning and image tiling are the same as in S820 in the first embodiment, so detailed will be omitted.

Step 831: Determining Whether or not Re-acquisition is Necessary (1)

The image processing unit 130 determines whether or not image re-acquisition is necessary according to the following procedures, and in a case where determination is made that re-acquisition is necessary, requests the data acquiring unit 110 for image reacquisition, and the flow advances to S811. In a case where determination is made that re-acquisition is unnecessary, the flow advances to S841. Detailed procedures of image re-acquisition necessity determination are the same as in S830 in the first embodiment, so detailed will be omitted.

Step 841: Saving Results (1)

The saving unit 135 transmits the examination date, information identifying the examinee eye, and the images acquired in S521, to the data server 40 in a correlated manner.

Step S851: Determining Whether or not to End Image Acquisition

The image processing unit 130 references the list of image acquisition parameters decided in S511, and in a case where there is an image not yet acquired in the list, the flow returns to S811 and image acquisition processing is continued. On the other hand, in a case where there are no images not yet acquired in the list, the image acquisition processing ends, and the flow advances to S531. Note that the image acquisition patterns are not restricted to that described in the present embodiment, and the present invention is also included in cases of acquiring the following image acquisition patterns as well.

Image acquisition patterns where multiple basic patterns are provided (multi-configuration type)

Image acquisition patterns where mid-magnification images are also included besides high-magnification images (multi-magnification type)

Image acquisition patterns defined as combinations of basic patterns (compound type)

Image acquisition patterns defined uniquely by user and registered (user-defined type)

Although a case has been described in the present embodiment where preregistered basic patterns are displayed on wide-angle images as the multiple types of high-magnification image acquisition parameters in multiple positions, with the user making a selection therefrom, the present invention is not restricted to this. For example, an arrangement may be made where a list is displayed of preregistered basic pattern names, as the multiple types of high-magnification image acquisition parameters, with the user selecting a desired basic pattern name therefrom. In the case of selecting a basic pattern name, a list display may be made of the image acquisition parameters stipulated by the selected basic pattern name, or information relating to image acquisition parameters including image acquisition position may be spatially laid out for a visual display. Alternatively, the color may be changed for each image type, to display information relating image acquisition parameters values and image acquisition positions.

According to the configuration described above, the information processing apparatus 10 performs the following processing on images taken by an SLO apparatus that acquires confocal images and non-confocal images at the same time. The operator decides acquisition conditions for the images by selecting from basic patterns registered beforehand regarding multiple types of high-magnification image acquisition parameters at multiple locations. Accordingly, multiple types of images of the eye that are crucial of observation and analysis can be efficiently acquired.

(Third Embodiment: Deciding Conditions relating to Acquisition of Images by Feature Regions in Images)

The information processing apparatus according to a third embodiment performs t following processing regarding confocal images Dcj of retinal blood vessels at generally the same imaging positions, and images (Dnr or Dnl) of non-confocal images Dnk taken of the retinal blood vessels with the aperture opened wide and taken from the right side of left side of the way the retinal blood vessels run. That is to say, the configuration has been made so that the more crucial parts images included for observation and measurement, based on image features or lesion candidate regions acquired in the images, the more types of images, or finer images are acquired. Specifically, confocal images Dcj and non-confocal images Dnk of retinal blood vessels such as illustrated in FIG. 6J are acquired. A case will be described where the more arteriovenous crossing portions, which are areas of predilection for retinal vein occlusion, are included in an image, the more types of images, or finer images are acquired.

FIG. 2B illustrates the configuration of apparatuses connected to the information processing apparatus 10 according to the present embodiment. The present embodiment differs from the first embodiment in that the information processing apparatus 10 is connected to a time phase data acquisition apparatus 50, in addition to the SLO imaging apparatus 20 and data server 40. The time phase data acquisition apparatus 50 is an apparatus that acquires biosignal data (time phase data) that autonomously and cyclically changes, such as a sphygmograph or electrocardiograph, for example. The time phase data acquisition apparatus 50 acquires time phase data Sj at the same time as acquiring images Dnk, in accordance with operations performed by an unshown operator. The acquired time phase data Sj is sent to the information processing apparatus 10 and data server 40. Note that the time phase data acquisition apparatus 50 may be directly connected to the SLO imaging apparatus 20. The light reception method of the SLO imaging apparatus 20 according to the present embodiment is configured such that the diameter and position of the aperture (pinhole) can be changed, so as to received as confocal signals as illustrated in FIG. 3C, or the diameter of the aperture can be enlarged and moved so as to receive as non-confocal signals as illustrated in FIG. 3D.

In addition to the wide-angle images Dlc and Dln and high-magnification images Dcj, Dnrk, and Dnlk of the examinee eye, and acquisition conditions such as the fixation target positions Fl and Fcn used at the time of acquisition, the data server 40 also holds image features of the eye. Any image features of the eye may be used, but the present embodiment handles retinal blood vessels and capillaries Q, and photoreceptor damage regions. The time phase data Sj output from the time phase data acquisition apparatus 50 and image features output from the information processing apparatus 10 are saved in the server. The time phase data Sj and image features of the eye are transmitted to the information processing apparatus 10 upon request by the information processing apparatus 10.

Next, FIG. 10 illustrates a functional block diagram of the information processing apparatus 10 according to the present embodiment. This configuration differs from the first embodiment with regard to the point that the data acquiring unit 110 has a time phase data acquiring unit 114, the deciding unit 131 has an image feature acquiring unit 1313, and the display control unit 134 does not include the image acquisition parameters presenting unit 1341. The image processing flow according to the present embodiment is the same as that illustrated in FIG. 5B. Other than S511, S521, and S531, the flow is the same as in the second embodiment, so just the processing of S511, S521, and S531 will be described in the present embodiment.

Step 511: Deciding Image Acquisition Parameters (2)

The data acquiring unit 110 acquires images of image feature acquisition. In the present embodiment, wide-angle images Dlc are acquired as images for feature acquisition. The method of acquisition of wide-angle images is the same as in the first embodiment, so description will be omitted. The image feature acquiring unit 1313 acquires retinal blood vessel regions and arteriovenous crossing portions as image features from the wide-angle images Dlc. The image processing unit 130 tentatively determines the preset values of image acquisition parameters based on image features acquired by the image feature acquiring unit 1313. In a case where the operator has specified constraint conditions (upper limit of total imaging time, etc.) or priority conditions (angle or imaging position to be give priority, etc.), the determining unit 1311 and imaging parameter deciding unit 1312 change the images that are the object of acquisitions, and the image acquisition parameters, to satisfy the constraint conditions and priority conditions. The image processing unit 130 also acquires individual image acquisition parameter values which the operator has specified as necessary, via the instruction acquiring unit 140. The determining unit 1311 determines final images that are the object of acquisition, based on preset values, constraint conditions, priority conditions, and individually specified parameter values, and the imaging parameter deciding unit 1312 decides the final image acquisition parameters.

Step 521: Acquiring Images (2)

The data acquiring unit 110 acquires high-magnification images and time phase data based on the image acquisition parameters decided in S511. Confocal images Dcj and non-confocal images Dnk are acquired following a retinal artery arcade A in the present embodiment, as illustrated in FIG. 6J. The time phase data acquiring unit 114 requests the time phase data acquisition apparatus 50 for time phase data Sj relating to biological signals. In the present embodiment, a sphygmograph serves as a time phase data acquisition apparatus, used to acquire pulse wave data Sj from the earlobe of the subject. This pulse wave data Sj is expressed with acquisition time on one axis and a cyclic point sequence having the pulse wave signal values measured by the sphygmograph on the other axis. The time phase data acquisition apparatus 50 acquires and transmits the time phase data Sj corresponding to the acquisition request. The time phase data acquiring unit 114 receives this pulse wave data Sj from the time phase data acquisition apparatus 50 via the LAN 30. The time phase data acquiring unit 114 stores the received time phase data Sj in the storage unit 120.

Now, there are two conceivable timings relating acquisition of the time phase data Sj by the time phase data acquisition apparatus 50; one is a case where the confocal data acquiring unit 111 or non-confocal data acquiring unit 112 starts image acquisition in conjunction with a particular phase of the time phase data Sj, the other is a case where acquisition of pulse wave data Pi and image acquisition are simultaneously started immediately after an image acquisition request. In the present embodiment, acquisition of time phase data Pi and image acquisition are simultaneously started immediately after an image acquisition request. The time phase data Pi of each image is acquired by the time phase data acquiring unit 114, the extreme value in each time phase data Pi is detected, and the cardiac cycle and relative cardiac cycle are calculated. The relative cardiac cycle is a relative value represented by a floating-point number between 0 and 1 where the cardiac cycle is 1.

The data acquiring unit 110 requests the SLO imaging apparatus 20 for acquisition of confocal images Dcj, non-confocal images Dnrk and Dnlk, and corresponding fixation target position data. In response to the request, the SLO imaging apparatus 20 acquires and transmits the confocal images Dcj, non-confocal images Dnrk and Dnlk, and corresponding fixation target position Fcn. The data acquiring unit 110 receives the confocal images Dcj, non-confocal images Dnrk and Dnlk, and corresponding fixation target position Fcn, from the SLO imaging apparatus 20 via the LAN 30, and stores these in the storage unit 120.

FIGS. 6C and 6D illustrate an example of a confocal image Dc and non-confocal image Dnr in a case of having photographed a retinal blood vessel. The confocal image Dc has strong reflection from the nerve fiber layer, so the background noise makes positioning difficult. The non-confocal image Dnr (Dnl) of the R channel (L channel) has higher contrast at the blood vessel wall at the right side (left side). The R channel image Dnr is also called a knife edge image, and may be used alone to observe retinal blood vessels including blood vessel walls.

Step 531: Display (2)

The display control unit 134 displays images acquired in S511 and S521 on the monitor 305. An image obtained by compositing the R channel image and L channel image is displayed composited in the monitor 305 using the positioning parameter values decided in S821. The type of images to be display is switched using a graphical user interface (GUI) that has been prepared for this purpose. Although radio buttons are used for switching in the present embodiment, any GUI arrangement may be used for the switching. The types of images to be switched are the two types of R channel images Dnr and L channel images Dnl. In a case of acquiring non-confocal images of multiple channels at generally the same time, the computing unit 133 may perform computation among inter-frame positioned images, and generate an image. For example, in a case of acquiring two types of non-confocal images at generally the same time, as in FIG. 3E or 3G for example, a) an added channel of an R channel image and L channel image using the R channel image Dnrk. and L channel image Dnlk, i.e., an image Dnr+l having (pixel values of the R channel image+pixel values of the L channel image) (FIG. 6E)

b) a Split Detector images Dns (FIG. 6F)

may be generated and displayed on the monitor 305 by the display control unit 134.

Next, the processing performed in S511 will be described in detail with reference to the flowchart in FIG. 7C.

Step 712: Tentative Setting of Image Acquisition Parameters by Image Features The data acquiring unit 110 acquires images for image feature acquisition. In the present embodiment, wide-angle images Dlc are acquired as images for image feature acquisition. Next, the image feature acquiring unit 1313 detects the retinal blood vessel regions and arteriovenous crossing portions as image features from the wide-angle images Dlc. The images from which image features are acquired are not restricted to wide-angle images, and cases of acquiring image features from acquired high-magnification images (Dcj or Dnk), for example, are also included in the present invention.

Retinal blood vessels have linear shapes, so the present embodiment employs a retinal blood vessel region detection method where a filter that enhances linear structures is used to extract the retinal blood vessels. Specifically, a wide-angle image Din is smoothed by a Gaussian function of a size σ equivalent to the radius of the arcade blood vessel, and thereupon a tube enhancement filter based on a Hessian matrix is applied, and binarization is performed at a threshold value Ta, thus extracting the arcade blood vessels. However, the detection method of arteriovenous crossing portions is not restricted to this, and any known retinal blood vessel extract technique may be used. As for the method for detecting arteriovenous crossing portions in the present embodiment, a crossing detection filter disclosed in Japanese Patent Laid-Open No. 2001-070247 is used. Specifically, a crossing portion is determined when there are four or more blood vessel regions at the perimeter of the filter, and there is a blood vessel region at the center portion of the filter. Retinal arteries contain more hemoglobin than retinal veins and thus are higher in luminance, so the lowest luminance value within each of the crossing blood vessel regions is calculated from the detected crossing portions, and in a case where the absolute value among the lowest luminance values is equal to or larger than a threshold value T1, this is determined to be an arteriovenous crossing. Note however, that the crossing detection method is not restricted to this, and any known crossing detection method may be used. Retinal veins tend to be lower with regard to luminance distribution of the intravascular space region (the region where blood flows), so in the, present invention, if the lowest luminance value in the intravascular space region in confocal images and non-confocal images is smaller than Tv, this is identified as a retinal vein in the present invention, and if Tv or larger, as a retinal artery.

Although description has been made in the present embodiment that the image feature acquiring unit 1313 acquires anatomical features such as arteriovenous crossing portions, the present invention is not restricted to this. For example, a lesion candidate region such as the photoreceptor defect portion Dc5 in FIG. 6K may be acquired as an image feature. Now, a lesion candidate region will also be referred to as a lesion region that is an example of a state of observation of an object, such as photoreceptors or the like. Although any detection method of the photoreceptor defect region may be used, detection is made in the present embodiment according to the following procedures. That is to say, Fourier transform is performed on the confocal images Dcj, a low-pass filter is applied to cut out high-frequency signal values, following which inverse Fourier transform is performed, and each region having a value smaller than a threshold T2 is detected as a photoreceptor defect region.

Next, the determining unit 1311 and imaging parameter deciding unit 1312 tentatively decide preset values of the image acquisition parameters based on image features acquired by the image feature acquiring unit 1313. For example, in a case of observing whether or not there is a major retinal blood vessel lesion such as blockage of retinal veins, an image of a retinal blood vessel region including retinal blood vessel walls is acquired. It is understood that arteriovenous crossing portions within three diameters worth of the optic disc Od from the center thereof are areas of predilection for blockage of retinal veins, and accordingly this is a portion crucial for observation. In order to accurately position images with a wide-angle image clearly observe retinal blood vessel walls on both sides, the confocal image Dc, R channel image Dnr, and L channel image Dnl need to be acquired. However, simply acquiring all types of images at all positions increases the acquisition time threefold, and the burden on the subject becomes problematic.

Accordingly, the determining unit 1311 determines to acquire the confocal image Dc, R channel image Dnr, and L channel image Dnl at positions including a retinal blood vessel region. Further, the imaging parameter deciding unit 1312 decides acquisition of the confocal images Dc at positions not including arteriovenous crossing portions within three diameters worth of the optic disc from the center thereof (the total of 24 positions indicated by dotted frames and single-line frames in FIG. 6.1) to be tentatively set to be performed according to (number of gradients, field angle, resolution, frame rate, number of seconds for acquisition)=(16 bits, 1.5°×1.5°, 400 pixels×400 pixels, 32 fps, 1 second). The R channel image Dnr is tentatively set to be acquired by (number of gradients, field angle, resolution, frame rate, number of seconds for acquisition)=(16 bits, 1.5°×1.5°, 400 pixels×400 pixels, 32 fps, 2 seconds). The L channel image Dnl is tentatively set to be acquired by (number of gradients, field angle, resolution, frame rate, number of seconds for acquisition)=(16 bits, 1.5°×1.5°, 400 pixels×400 pixels, 32 fps, 2 seconds). The confocal image Dc here is not for observation and measurement, but is an image used for tiling as to the wide-angle image Dc, so the number of frames does not have to be very large.

Further, acquisition of confocal images Dc at positions including arteriovenous crossing portions within three diameters worth of the optic disc from the center thereof (the total of 2 places indicated by double-line frames in FIG. 6J) is decided to be tentatively set to be performed according to (number of gradients, field angle, resolution, frame rate, number of seconds for acquisition)=(16 bits, 1.5°×1.5°, 400 pixels×400 pixels, 32 fps, 1 second). The R channel image Dnr and L channel image Dnl are tentatively set to be acquired by (number of gradients, field angle, resolution, frame rate, number of seconds for acquisition)=(16 bits, 1.5°×1.5°, 400 pixels×400 pixels, 32 fps, 4 seconds).

Simply taking 4 seconds to acquire all channel images at all acquisition positions for acquisition of high-magnification images requires 26 locations×(4+4+4) seconds=312 seconds, but the present embodiment only requires 24 locations×(1+2+2) seconds+2 locations×1+4+4) seconds=138 seconds.

Step 722: Setting Constraint and Priority Conditions

In a case where the operator has specified constraint conditions (upper limit of total imaging time, etc.) or priority conditions (angle or imaging position to be give priority, etc.), the determining unit 1311 and imaging parameter deciding unit 1312 change the images that are the object of acquisitions, and the image acquisition parameters, to satisfy the constraint conditions and priority conditions. The image processing unit 130 also acquires individual image acquisition parameter values which the operator has specified as necessary, via the instruction acquiring unit 140.

In the present embodiment, the operator sets the upper limit of total imaging time to 60 seconds. Also, i) hold image acquisition parameters at positions including arteriovenous crossing portions within three diameters worth of the optic disc from the center thereof ii) order of priority regarding availability of acquisition of image types is R channel image, L channel image, confocal image, in that order from high priority to low are set as priority conditions. Further, i) has higher priority of ii). While the acquisition time of images was a total of 138 seconds for 26 locations in S712, instruction is given here to set the upper limit value for the total imaging time to 60 seconds, while holding image types and image acquisition parameters as much as possible at positions including arteriovenous crossing portions within three diameters worth of the optic disc from the center thereof. The determining unit 1311 and the parameter deciding unit 1312 change the images to be acquired and the image acquisition parameters so that the priority conditions and the upper limit value are satisfied. In other words, determination is made by the determining unit 1311 that a confocal image Dc, R channel image Dnr, and L channel image Dnl need to be acquired at positions including arteriovenous crossing portions within three diameters worth of the optic disc from the center thereof, but only the R channel image Dnr needs to be acquired at positions not including arteriovenous crossing portions within three diameters worth of the optic disc from the center thereof. The imaging parameter deciding unit 1312 decides to change the acquisition time for R channel images at positions not including arteriovenous crossing portions within three diameters worth of the optic disc from the center thereof to 1.75 seconds, while maintaining the image acquisition parameters of images including arteriovenous crossing portions. Accordingly, the total acquisition time for images is reduced to 24 locations×(0+1.75+0) seconds+2 locations×1+4+4) seconds=60 seconds while maintaining the image acquisition parameters of images including arteriovenous crossing portions, that are crucial for observation. In light of the fact that if the same number of sects are used for acquisition of all types of images at all acquiring positions when the upper limit of the total acquisition time is 60 seconds each moving image can only be acquired for 0.77 seconds, the proposed technique can efficiently acquire various types of images of the eye that are crucial for observation.

Although description has been made primarily relating to changing parameters relating to time, to facilitate understanding, parameters to be changed are not restricted to this, and any type of parameter may be changed. Also, an arrangement where image acquisition parameters are tentatively decided in S712, after the image processing unit 130 having acquired acquisition necessity and acquisition parameter values individually changed by the operator as necessary, via the instruction acquiring unit 140, and the image acquisition parameters are overwritten to decide final image acquisition parameters, is also included in the present invention.

Step 732: Deciding Image Acquisition Parameters

The determining unit 1311 determines images that are the object of acquisition based on the following information, and the imaging parameter deciding unit 1312 decides the image acquisition parameters.

Preset values of image acquisition parameters corresponding to the image acquisition pattern selected by the operator in S712

Constraint conditions and priority conditions the operator instructed as necessary in S722

Individual image acquisition parameters values the operator has changed as necessary in S722

In the present embodiment, determining unit 1311 determines that a confocal image Dc, R channel image Dnr, and L channel image Dnl are to be acquired at positions including arteriovenous crossing portions within three diameters worth of the optic disc from the center thereof at the image acquisition patter in FIG. 6J, but only the R channel image Dnr is to be acquired at positions not including arteriovenous crossing portions.

The imaging parameter deciding unit 1312 decides, for positions not including arteriovenous crossing portions within three diameters worth of the optic disc from the center thereof (the total of 24 positions indicated by dotted frames and single-line frames in FIG. 6J) R channel images Dnr are to be acquired at (number of gradients, field angle, resolution, frame rate, number of seconds for acquisition)= (16 bits, 1.5°×1.5°, 400 pixels×400 pixels, 32 fps, 1.75 seconds).

For positions including arteriovenous crossing portions within three diameters worth of the optic disc from the center thereof (the total of 2 places indicated by double-line frames in FIG. 6J), the imaging parameter deciding unit 1312 tentatively decides that acquisition of confocal images Dcj is performed at (number of gradients, field angle, resolution, frame rate, number of seconds for acquisition)= (16 bits, 1.5°×1.5°, 400 pixels×400 pixels, 32 fps, 1. second). Also, the imaging parameter deciding unit 1312 tentatively decides that R channel images Dnr and L channel images Dnl are to each be acquired at (number of gradients, field angle, resolution, frame rate, number of seconds for acquisition)=(16 bits, 1.5°×1.5°, 400 pixels×400 pixels, 32 fps, 1.75 seconds).

Next, the processing performed in S521 will be described in detail with reference to the flowchart in FIG. 8B.

Step 811: Acquiring Images and Related Data (2)

The data acquiring unit 110 acquires images based on the image acquisition parameters decided in S511. Detailed procedures of image acquisition are the same as in S521 and in S810 in the first embodiment, so detailed will be omitted.

Step 821: Positioning Images (2)

The positioning unit 132 performs positioning of image s acquired in S811. Detailed procedures of inter-frame positioning and image tiling are the same as in S820 in the first embodiment, so detailed will be omitted. Note however, in the present embodiment, the positioning unit 132 performs inter-frame positioning for each of the image types (Dcj, Dnr, and Dnl). Composited images are generated for the image types (Dcj, Dnr, and Dnl). Composited images are generated according to the following procedures to avoid change in the shape of the blood vessels among frames due to influence of the heartbeat when observing retinal blood vessel walls. That is to say, instead of averaging all frames, just frames correlated with pulse wave signals belonging to a particular phase interval are selected and composited. In the present embodiment, the phase intervals of pulse waves are divided into five intervals, and the frames belonging to the interval including the phase where the pulse wave signal value is minimal are selected and composited. However, the frame selection method is not restricted to this, and any selection method can be used yields the effects of eliminating the influence of the heartbeat can be used. For the image tiling, the positioning unit 132 performs tiling of the image types (Dcj, Dnr, and Dnl) as to the wide-angle image Dlc. Further, the positioning unit 132 performs inter-image positioning among the various types of composited images at each acquisition position. Thus, the relative position among image types at generally the same acquisition position is calculated.

Step 831: Determining Whether or not Re-acquisition is Necessary (2)

This is the same as S831 in the second embodiment, so description will be omitted.

Step 841: Saving Results (2)

The saving unit 135 transmits the examination date, information identifying the examinee eye, images acquired in S521, pulse wave data, and the positioning parameter values to the data server in a correlated manner. Although description has been made in the present embodiment regarding acquiring retinal blood vessel regions and arteriovenous crossing portions as image features, the image acquisition parameters may be decided based on lesion candidate region such as photoreceptor defect regions acquired by the image feature acquiring unit 1313 from confocal images as image features. It is generally understood that photoreceptors become defective from the outer segments, next become defective at the inner segments, and finally reach necrosis. NPL 2 describes that confocal images Dcj enable photoreceptor outer segment defects to be observed, while non-confocal images Dnk enable photoreceptor inner segment defects to be observed. Accordingly, it can be understood that photoreceptor defect regions in confocal images and Split Detector images at the same imaging position are important for observation and analysis of the level of the photoreceptor lesion. Specifically, the determining unit 1311 determines that acquisition of a mid-magnification image Dc2o of the macular area is necessary, and the imaging parameter deciding unit 1312 decides to acquire the mid-magnification image Dc2o at (number of gradients, field angle, resolution, frame rate, number of seconds for acquisition)=(16 bits, 3°×3°, 800 pixels×800 pixels, 32 fps, 1 second).

After the data acquiring unit 110 has acquired the mid-magnification image Dc2o each acquisition position that has been decided, the image feature acquiring unit 1313 detects photoreceptor defect regions in each mid-magnification image Dc2o. In a case where no photoreceptor defect region is detected, the flow advances to confocal image acquisition of the mid-magnification image at the next acquisition position. In a case where a photoreceptor defect region has been detected, the determining unit 1311 determines that there is a need to acquire a high-magnification confocal image Dc1m at the same acquisition position, and corresponding high-magnification image nonconfocal images Dnr and Dnl. The imaging parameter deciding unit 1312 decides to acquire the high-magnification confocal image Dc1m at (number of gradients, field angle, resolution, frame rate, number of seconds for acquisition)=(16 bits, 1.5°×1.5°, 800 pixels×800 pixels, 32 fps, 3 seconds). Decision is also made to acquire the high-magnification non-confocal images Dnr and Dnl at generally the same acquisition position at (number of gradients, field angle, resolution, frame rate, number of seconds for acquisition)=(16 bits, 1.5°×1.5°, 800 pixels×800 pixels, 32 fps, 2 seconds).

The data acquiring unit 110 acquires the high-magnification images Dc1m, Dnr, and Dnl with the decided image acquisition parameters. Note that the image acquisition parameters may be decided for the high-magnification images based on photoreceptor defect regions acquired from wide-angle images Dlc instead of mid-magnification images Dc2o. According to the above configuration, the information processing apparatus 10 performs the following processing on a confocal image Dcj acquired at generally the same position and on non-confocal images Dnk with the diameter of the aperture enlarged and moved to the right and left. That is to say, the more crucial parts of images included for observation and measurement, based on image features or lesion candidate regions (lesion region which is an example of a state to be observed) acquired in the image, the more types of images, or finer images are acquired. Accordingly, multiple eye images crucial in observation and analysis can be efficiently acquired.

(Fourth Embodiment: Deciding Conditions for Image Acquisition Based on Acquisition Results by Examination Date)

The information processing apparatus according to the present embodiment is configured such that, in a case where multiple types of images have been acquired on different examination dates, the more examination dates on which an image has been acquired, the more that image is an object of acquisition in the present examination, and acquisition is performed with generally the same parameters. The configuration of apparatuses connected to the information processing apparatus 10 according to the present embodiment is as illustrated in FIG. 2A, and differs from the third embodiment with regard to the point no time phase data acquisition apparatus 50 is connected. The functional block configuration of the information processing apparatus 10 according to the present embodiment differs from that in the third embodiment with regard to the points that the data acquiring unit 110 does not have the time phase data acquiring unit 114 and image feature acquiring unit 1313, and the positioning unit 131 includes a conformability calculating unit 1314. This also differs from the third embodiment with in that the data acquiring unit 110 acquires examination data of different examination dates. The confocal signal and non-confocal signal reception method at the SLO imaging apparatus 20 according to the present embodiment is the same as in the first and second embodiments, in that the configuration is made to receive confocal signals and two channels of non-confocal signals, as illustrated in FIG. 3E.

The image processing flow according to the present embodiment is illustrated in FIG. 5B, and is the same as the third embodiment except for S511, S521, and S531. Accordingly, S511, S521, and S531 will be described in the present embodiment. Note that in the present embodiment, confocal images and non-confocal images from past examinations are written as Dcjf and Dnkf respectively (where f=1, 2, ... , e−1, f being a natural number indicating the No. of the examination in serial order), and confocal images and non-confocal images from past examinations are written as Dcje and Dnke, respectively.

Step 511: Deciding Image Acquisition Parameters (3)

Upon the attribute data acquiring unit 113 having acquired attribute data for all examination images, and the conformability calculating unit 1314 having calculating the conformability with past examination images, the determining unit 1311 and image processing method deciding unit 1312 decide images for generating and image. generating method, based on the conformability. In a case where the operator has specified constraint conditions (upper limit of total imaging time, etc.) or priority conditions (angle or imaging position to be give priority, etc.), the determining unit 1311 and imaging parameter deciding unit 1312 change the images that are the object of acquisitions, and the image acquisition parameters, to satisfy the constraint conditions and priority conditions. The image processing unit 130 also acquires individual image acquisition parameter values which the operator has specified as necessary, via the instruction acquiring unit 140. The determining unit 1311 determines final images that are the object of acquisition, based on the tentatively decided image acquisition parameters, constraint conditions, priority conditions, and individually specified parameter values, and the imaging parameter deciding unit 1312 decides the final image acquisition parameters. Specifics of the image acquisition parameter deciding processing will be described in detail in S713, S723, S733, and S743.

Step 521: Acquiring Images (3)

The data acquiring unit 110 requests the SLO imaging apparatus 20 for acquisition of wide-angle images Dlce, confocal images Dcje and non-confocal images Dnke, and fixation target positions Fie and Fcne corresponding to the current examination, based on the image acquisition parameters decided in S511. In the present embodiment, the wide-angle images Dlce, confocal images Dcje, and non-confocal images Dnke are acquired with fixation target positions Fle at the fovea and fixation target positions Fcne at the fovea and parafovea. Note that the imaging position setting method is not restricted to this, and the imaging position may be set to an optional position. The SLO imaging apparatus 20 acquires and transmits the wide-angle images Dlce, confocal images Dcje and non-confocal images Dnke, and fixation target position Fle and fixation target position Fcne, in response to the acquisition request. The data acquiring unit 110 receives the wide-angle images Dlce, confocal images Dcje, non-confocal images Dnke, and fixation target position Fle and fixation target position Fcne, from the SLO imaging apparatus 20 via the LAN 30. The data acquiring unit 110 stores the received wide-angle images Dlce, confocal images Dcje, non-confocal images Dnke, and fixation target positions Fle and Fcne in the storage unit 120.

Step 531: Display (3)

The display control unit 134 displays the images acquired in S521 on the monitor 305. The computing unit 133 in the present embodiment performs computation among inter-frame-positioned R channel images and L channel images, and generates a composited image of Split Detector images and the display control unit 134 displays on the monitor 305. Next, the processing performed in S511 will be described in detail with reference to the flowchart illustrated in FIG. 7D.

Step 713: Acquiring Attribute Information of All Examination Images

The attribute data acquiring unit 113 acquires attribute data relating to the past examination images. Attribute data in the present embodiment is date of image acquisition, position of acquisition, focus position, image type (confocal/R channel/L channel/optional inter-image-type computation), number of gradations, field angle, resolution, frame rate, and number of seconds of acquisition.

Step 723: Calculating Inter-Examination Conformability

The conformability calculating unit 1314 calculates conformability with past examination images for each image, based on the attribute data of all past examination images. In the present embodiment, conformability of the current examination images as to the past examination images is calculated by $\omega_3 \times Ib + \omega_4 \times \Sigma Ien$, at each acquisition position. Ib here is a value (0 or 1) representing whether or not there is an image generated with the same attributes other than the date of acquisition in a reference examination (baseline). Ien is calculated by (value (0 or 1) representing whether or not there is an image having the same attributes other than the date of acquisition in each examination)/(total number of past examinations). $\Sigma$ represents the summation of all past examinations. $\omega_3$ and $\omega_4$ are weighting parameters that can be given optional values in the range of 0 to 1. Both are 0.5 in the present embodiment. The deciding unit 131 decides the image acquisition parameters based on the conformability. In the present embodiment, the positioning unit 131 tentatively decides to acquire images having image attributes where the conformability calculated at each acquisition position is equal to or larger than a threshold T3. The calculation method for conformability is not restricted to this; any calculation method may be used as long as indices are calculated suitable for determining that the more examination dates on which an image has been acquired, the more that image is an object of acquisition in the present examination.

Step 733: Manually Adjusting Image Acquisition Parameters

The image processing unit 130 acquires individual image acquisition parameter values changed by the operator as necessary via the instruction acquiring unit 140. Although described in the present embodiment that the user does not particularly manually modify individual image acquisition parameter values, any image acquisition parameters may be modified.

Step 743: Deciding Image Acquisition Parameters

The determining unit 1311 determines images that are the object of acquisition based on the following information, and the imaging parameter deciding unit 1312 decides the image acquisition parameters.

Image acquisition parameters tentatively decided based on inter-examination conformability calculated in S723

Individual image acquisition parameters values the operator has changed as necessary in S733

Next, the processing performed in S521 will be described in detail with reference to the flowchart in FIG. 8B.

Step 811: Acquiring Images and Related Data (3)

The data acquiring unit 110 acquires images based on the image acquisition parameters decided in S511. Detailed procedures of image acquisition are the same as that described in in S521 and in S810 in the first embodiment, so description will be omitted.

Step 821: Positioning Images (3)

The positioning unit 132 performs inter-frame positioning and tiling as to the wide-angle image Dlce, confocal image Dcje, and non-confocal images Dnke of the present examination. Specific inter-frame positioning and image tiling procedures as the same as in S520 of the first embodiment, so description will be omitted.

Step 831: Determining Whether or not Re-acquisition is Necessary (3)

This is the same as S831 in the second embodiment, so description will be omitted.

S841: Saving Results

The saving unit 135 transmits examination date, information identifying the examinee eye, and the images acquired in S521, to the data server 40 in a correlated manner.

Step 851: Determining Whether or not to End Image Acquisition

The image processing unit 130 references the image acquisition parameters decided in S511. In a case where there is an image not yet acquired, the flow returns to S811 and image acquisition processing is continued. On the other hand, in a case where there are no images not yet acquired, the image acquisition processing ends, and the flow advances to S531.

According to the configuration described above, in a case where multiple types of images have been acquired on different examination dates, the information processing apparatus 10 determines that the more examination dates on which an image has been acquired, the more that image is an object of acquisition in the present examination, and acquisition is performed with generally the same parameters. Accordingly, multiple types of eye images crucial for comparative observation and measurement among images of different examination dates can be efficiently acquired.

(Other Embodiments)

Although description has been made in the above embodiments that the data acquiring unit 110 includes both the confocal data acquiring unit 111 and the non-confocal data acquiring unit 112, the data acquiring unit 110 does not need to include the non-confocal data acquiring unit 112, as long as the configuration enables acquisition of two or more types of non-confocal data.

Although description has been made in the above embodiments where image acquisition position, field angle, resolution, number of gradients, frame rate, number of seconds for acquisition, and order of acquisition, are conditions relating to acquisition of multiple types of high-magnification images, conditions relating to acquisition of multiple types of high-magnification images are not restricted to these. Focus position, and the number of images in a case where the same image acquisition position is repeatedly imaged (number of times of repeated imaging) are also included in the conditions. For example, an arrangement may be made where the more of image features crucial for observation and analysis (anatomical features or lesion candidate regions) that the image feature acquiring unit 1313 has detected in an image, image acquisition is performed for more focal positions thereof or a greater number of images is acquired.

An example of conditions relating to acquisition is imaging conditions (imaging parameters) for imaging an eye when acquiring confocal images and non-confocal images. Examples thereof include acquisition position, field angle, resolution, frame rate, and so on. Another example of conditions relating to acquisition is signal processing conditions (signal processing parameters) for processing signals obtained by detecting returning light from an eye when acquiring confocal images and non-confocal images. Another example of conditions relating to acquisition is analysis processing conditions (analysis processing parameters) for analyzing confocal images and non-confocal images.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-093539, filed Apr. 30, 2015, which is hereby incorporated by reference herein in its entirety.

The invention claimed is:

1. An ophthalmologic imaging apparatus that acquires a plurality of types of images of an eye including a confocal image and a non-confocal image of the eye, the confocal image and the non-confocal image being obtained with a common light source, the ophthalmologic imaging apparatus comprising:
    a deciding unit configured to decide conditions relating to acquisition of the plurality of types of images, for each type of the plurality of types of images; and
    a control unit configured to control the ophthalmologic imaging apparatus to acquire at least one of the plurality of types of images, in accordance with the decided conditions.

2. The ophthalmologic imaging apparatus according to claim 1, further comprising:
    a specifying unit configured to specify a imaging position of the eye,
    wherein the deciding unit decides conditions relating to the acquisition, based on the specified imaging position.

3. The ophthalmologic imaging apparatus according to claim 2, wherein, in a case where a photoreceptor of the eye is specified as the imaging position, the deciding unit decides the conditions relating to acquisition so that the number of frames acquired of the confocal image is larger than the number of frames acquired of the non-confocal image.

4. The ophthalmologic imaging apparatus according to claim 2, wherein, in a case where a blood vessel of the eye is specified as the imaging position, the deciding unit decides the conditions relating to acquisition so that the number of frames acquired of the confocal image is smaller than the number of frames acquired of the non-confocal image.

5. The ophthalmologic imaging apparatus according to claim 1, further comprising:
    an analyzing unit configured to analyze the confocal image,
    wherein the deciding unit decides the conditions relating to acquisition, based on a state of an object of observation obtained by analyzing the confocal image.

6. The ophthalmologic imaging apparatus according to claim 5, wherein in a case there is a lesion region as the state of the object of observation, the deciding unit decides the conditions relating to acquisition, to further acquire the non-confocal image.

7. The ophthalmologic imaging apparatus according to claim 1, further comprising:
    a specifying unit configured to specify a basic pattern indicating distribution of positions of acquisition of the plurality of types of images,
    wherein the deciding unit decides the conditions relating to acquisition based on the specified basic pattern.

8. The ophthalmologic imaging apparatus according to claim 1, further comprising:
    an image feature acquiring unit configure to analyze a low-magnification image of the eye and acquire information of image features of the low-magnification image, wherein the deciding unit decides conditions related to acquisition of multiple types of high-magnification image of the eye, based on the acquired information.

9. The ophthalmologic imaging apparatus according to claim 1, wherein the deciding unit decides the conditions relating to acquisition based on at least of one of anatomical features and lesion candidates in the confocal image.

10. The ophthalmologic imaging apparatus according to claim 1, wherein the deciding unit decides the conditions relating to acquisition based on conformability as to attributes of images acquired in past examinations.

11. The ophthalmologic imaging apparatus according to claim 1, wherein the deciding unit decides imaging conditions for imaging the eye at the time of acquiring the confocal image and non-confocal image, as the conditions relating to acquisition.

12. The ophthalmologic imaging apparatus according to claim 1, wherein the deciding unit decides signal processing conditions for processing signals obtained by detecting returning light from the eye when acquiring the confocal image and non-confocal image, as the conditions relating to acquisition.

13. The ophthalmologic imaging apparatus according to claim 1, wherein the deciding unit decides analyzing conditions for analyzing the confocal image and non-confocal image, as the conditions relating to acquisition.

14. The ophthalmologic imaging apparatus according to claim 1, wherein the acquisition position of the confocal image and the acquisition position of the non-confocal image in the eye are the same.

15. The ophthalmologic imaging apparatus according to claim 1, wherein multiple types of images acquired by imaging the eye at generally the same time by controlling the ophthalmologic imaging apparatus are transmitted to an information processing apparatus communicably connected to the ophthalmologic imaging apparatus.

16. The ophthalmologic imaging apparatus according to claim 1, further comprising:
the common light source configured to acquire a confocal image and a non-confocal image of the eye;
an optical member configured to split returning light from the eye irradiated by light from the common light source, into returning light passing through a confocal region and returning light passing through a non-confocal region; and
an image acquiring unit configured to acquire the confocal image based on the returning light passing through the confocal region, and acquires the non-confocal image based on the returning light passing through the non-confocal region.

17. The ophthalmologic imaging apparatus according to claim 16, further comprising:
a mechanism to adjust at least one of a position and a shape of an aperture disposed upstream of a light-receiving portion that receives light of at least one of returning light passing through the confocal region and returning light passing through the non-confocal region.

18. The ophthalmologic imaging apparatus according to claim 1, wherein the confocal image and the non-confocal image are obtained with an optical member that splits returning light from the eye irradiated by light from the common light source.

19. The ophthalmologic imaging apparatus according to claim 1, wherein the confocal image and the non-confocal image are obtained with a common adaptive optics system.

20. The ophthalmologic imaging apparatus according to claim 1, wherein the confocal image and the non-confocal image are obtained with a common focus lens.

21. The ophthalmologic imaging apparatus according to claim 1, wherein the confocal image and the non-confocal image are obtained with a common scanning optical system.

22. An ophthalmologic imaging apparatus that acquires a plurality of types of images of an eye including a confocal image and a non-confocal image of the eye, the confocal image and the non-confocal image being obtained with a common light source, the ophthalmologic imaging apparatus comprising:
a deciding unit configured to independently decide conditions relating to acquisition of the confocal image and the non-confocal image.

23. The ophthalmologic imaging apparatus according to claim 22, wherein the deciding unit independently decides the conditions, such that at least one condition of number of frames and number of gradients differs when acquiring the confocal image and non-confocal image, based on an observation position of the eye.

24. The ophthalmologic imaging apparatus according to claim 23, wherein the deciding unit decides the number of frames acquired of the confocal image to be larger than the number of frames acquired of the non-confocal image in a case where a photoreceptor of the eye has been specified as the observation position, and the number of frames acquired of the confocal image to be smaller than the number of frames acquired of the non-confocal image in a case where a blood vessel of the eye has been specified as the observation position.

25. The ophthalmologic imaging apparatus according to claim 22, wherein the confocal image and the non-confocal image are obtained with an optical member that splits returning light from the eye irradiated by light from the common light source.

26. The ophthalmologic imaging apparatus according to claim 22, wherein the confocal image and the non-confocal image are obtained with a common adaptive optics system.

27. The ophthalmologic imaging apparatus according to claim 22, wherein the confocal image and the non-confocal image are obtained with a common focus lens.

28. The ophthalmologic imaging apparatus according to claim 22, wherein the confocal image and the non-confocal image are obtained with a common scanning optical system.

29. The ophthalmologic imaging apparatus according to claim 22, wherein the deciding unit decides processing conditions for processing signals obtained by detecting returning light from the eye when acquiring the confocal image and non-confocal image, as the conditions relating to acquisition.

30. The ophthalmologic imaging apparatus according to claim 22, wherein the deciding unit decides analyzing conditions for analyzing the confocal image and non-confocal image, as the conditions relating to acquisition.

31. An operation method of an ophthalmologic imaging apparatus that acquires a plurality of types of images of an eye including a confocal image and a non-confocal image of the eye, the confocal image and the non-confocal image being obtained with a common light source, the method comprising:
a step of deciding conditions relating to acquisition of the plurality of types of images, for each type of the plurality of types of images; and
a step of controlling the ophthalmologic imaging apparatus to acquire at least one of the plurality of types of images, in accordance with the decided conditions.

32. A non-transitory computer-readable storage medium storing a program causing a computer to execute the operation method of an ophthalmologic imaging apparatus according to claim 31.

33. An operation method of an ophthalmologic imaging apparatus that acquires a plurality of types of images of an eye including a confocal image and a non-confocal image of the eye, the confocal image and the non-confocal image being obtained with a common light source, the method comprising:
   a step of independently deciding conditions relating to acquisition of the confocal image and the non-confocal image, and
   a step of controlling the ophthalmologic imaging apparatus to acquire at least one of the plurality of types of images in accordance with the decided conditions.

34. A non-transitory computer-readable storage medium storing a program causing a computer to execute the operation method of an ophthalmologic imaging apparatus according to claim 33.

* * * * *